United States Patent
Khan

(10) Patent No.: US 7,741,112 B2
(45) Date of Patent: Jun. 22, 2010

(54) VECTOR MEDIATED ORGANELLE TRANSFECTION

(75) Inventor: Shaharyar M. Khan, North Garden, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 342 days.

(21) Appl. No.: 10/498,328

(22) PCT Filed: Dec. 12, 2002

(86) PCT No.: PCT/US02/39745

§ 371 (c)(1), (2), (4) Date: Jul. 18, 2006

(87) PCT Pub. No.: WO03/052067

PCT Pub. Date: Jun. 26, 2003

(65) Prior Publication Data

US 2007/0011759 A1     Jan. 11, 2007

Related U.S. Application Data

(60) Provisional application No. 60/340,338, filed on Dec. 13, 2001.

(51) Int. Cl.
*C12N 15/63* (2006.01)
*C12N 5/00* (2006.01)
(52) U.S. Cl. .................... 435/325; 435/320.1
(58) Field of Classification Search .............. 436/4; 435/320.1, 325
See application file for complete search history.

(56) References Cited

U.S. PATENT DOCUMENTS

| 5,831,020 | A |   | 11/1998 | Citovsky |           |
|-----------|---|---|---------|----------|-----------|
| 5,854,414 | A | * | 12/1998 | Hillman et al. | ............ 536/23.5 |

| 2007/0011759 | A1 | 1/2007 | Khan |

FOREIGN PATENT DOCUMENTS

| CA | 2272788        | 12/2000 |
| WO | WO 98/46271 A1 | 10/1998 |
| WO | WO 00/19993 A1 | 4/2000  |

OTHER PUBLICATIONS

Shore et al, (Eur J Biochem, 227: 9-18, 1995.*
Ghosh et al, (Gene Expr, 7(3): 1-2, 1998.*
Owen et al, (Human Gene Therapy, 11: 2067-2078, 2000.*
de Grey et al, (TIBTECH, 18: 394-399, 2000).*
Tommassen et al, (Mol Gen Genet , 197: 503-508, 1984).*
D'Souza, G. , et al., "Gene Therapy of the other Genome : The Challenges of treating Mitochondrial DNA Defects", *Pharm Res.,* 24(2), Epub Dec. 19, 2006,(Feb. 2007),228-38.
Khan, S. M., et al., "Development of mitochondrial gene Replacement Therapy", *J Bioenerg Biomembr.,* 36(4), XP019280561,(Aug. 2004),387-93.
Maliga, P. , et al., "Plant biotechnology 2007: all three genomes make contributions to progress", *Current Opinion in Biotechnology,* 18(2), (Apr. 17, 2007),97-99.
Wallace, D. C., et al., "The mitochondrial genome in human adaptive radiation and disease: on the road to therapeutics and performance enhancement.", *Gene,* 354, XP005019916,(Jul. 18, 2005),169-80.

* cited by examiner

*Primary Examiner*—Anne-Marie Falk
*Assistant Examiner*—Magdalene K Sgagias
(74) *Attorney, Agent, or Firm*—Schwegman, Lundberg & Woessner, P.A.

(57) ABSTRACT

The present invention provides compositions and methods for direct transfection of mitochondria and chloroplast DNA in living cells. More particularly, the present invention is based on the use of viral vectors that specifically bind to receptors uniquely found on the target organelle. In one embodiment, as shown in FIG. 1, a eukaryotic cell containing an organelle (1) that has been modified to express a viral receptor (2) on the organelle's surface is provided. A viral vector (6) comprising a desired recombinant DNA construct (3) is introduced into the cytosol of the cell, wherein the viral vector binds to its receptor and introduces the recombinant DNA into the interior of the organelle.

4 Claims, 5 Drawing Sheets

Replication and Transcription of Mitochondrial DNA

US 7,741,112 B2

VECTOR MEDIATED ORGANELLE TRANSFECTION

RELATED APPLICATIONS

This application is a national stage filing of International Application No. PCT/US02/39745, filed Dec. 12, 2002, which claims priority under 35 U.S.C. §119(e) to U.S. Provisional Patent Application No. 60/340,338, filed on Dec. 13, 2001, the disclosure of which is incorporated herein by reference in its entirety.

US GOVERNMENT RIGHTS

This invention was made with United States Government support under Grant No. NIH NS39005 and NIH NS39788 awarded by National Institutes of Health. The United States Government has certain rights in the invention.

FIELD OF THE INVENTION

The present invention is directed to a compositions and methods of transfecting organelles, in particular mitochondria and chloroplasts.

BACKGROUND OF THE INVENTION

Mitochondria are the sole energy-producing organelles in all eukaryotic cells, and therefore play a critical role in maintaining proper cellular bioenergetics, homeostatic levels and cellular life cycles. Similarly, chloroplasts are also efficient ATP-producing machines that use light as the source of energy rather than sugars or fatty acids. Both mitochondria and chloroplasts contain multiple copies of organelle DNA that is replicated and transcribed in the organelles. In mammals, mitochondrial DNA (mtDNA) is a circular, approximately 16.5 kilobase, intronless genome that encodes 13 electron transport chain (ETC) proteins, 2 ribosomal RNA's and 22 tRNA's. Most insights into mitochondrial genetics have come in yeast, where biolistic transformation allows for engineering of mitochondrial replicons. However, many features of mammalian mitochondrial gene expression and respiratory chain biogenesis are not reproducible in yeast.

In mammals, cytoplasmic fusion and microinjection are used to introduce donor mitochondria, but these techniques fail to provide a mechanism for the direct manipulation of mtDNA. In addition the uptake of exogenous DNA into mitochondria involving the protein import pathway has been reported from two laboratories. Vestweber and Schatz ([1989] Nature (London) 338:170-172) achieved uptake of a 24 bp both single-and double-stranded oligonucleotide into yeast mitochondria by coupling the 5' end of the oligonucleotide to a precursor protein consisting of the yeast cytochrome c oxidase subunit IV presequence fused to a modified mouse dihydrofolate reductase. More recently, Seibel et al. (1995, Nucleic Acids Research 23:10-17) reported the import into the mitochondrial matrix of double-stranded DNA molecules conjugated to the amino-terminal leader peptide of the rat ornithine-transcarbamylase. Both studies, however, were done with isolated mitochondria, not addressing the question of how oligonucleotide-peptideconjugates will pass the cytosolic membrane and reach mitochondrial proximity. U.S. Pat. No. 6,171,863 discloses the use of dequalinium-DNA complexes as a vehicle for delivering DNA to the interior of cells and potentially to the mitochondria Because the DNA is associated with dequalinium, the resulting complex has a positive charge. The positively charged complex is attracted to negatively charged compartments. Thus, US Pat. No. 6,171,863 discloses delivery of DNA to negatively charged compartments, and does not disclose the specific delivery DNA to mitochondria or chloroplasts. Indeed, no technique has been disclosed for targeting specific organelles, for example the chloroplast or mitochondria, for the delivery of nucleic acids using a receptor:ligand mechanism.

Thus the inability to specifically manipulate the chloroplast and mitochondrial genome has hampered researchers' efforts to fully understand chloroplast and mtDNA replication, transcription, and translation processes. The ability to specifically manipulate mtDNA and introduce it into living cells would greatly enhance researchers' ability to fully investigate the function of individual chloroplast/mitochondrial genes and overall chloroplast/mitochondrial function.

Furthermore, the ability to manipulate the mitochondrial genome also provides a novel method of treating diseases associated with defective mitochondrial function. With age, the function of mitochondria decreases with a marked increase of mutations and large deletions of mtDNA. In particular, oxidative damage increases with age, often leading to a higher rate of mtDNA mutations. Aside from known mtDNA mutations, several forms of cancer and neurodegeneration are associated with mutations in mtDNA. For example, mutations in mitochondrial DNA are the suspected cause of a host of degenerative neurological diseases including Alzheimers, Parkinsons and adult-onset diabetes. These mutations result in decreased electron transport chain efficiency, and the build-up of mtDNA deletions due to free radical damage (aging).

In addition, given the bioenergetic functions of chloroplasts, the ability to introduce exogenous genes or otherwise manipulate the chloroplast genome could have a tremendous impact on increasing the vitality and yields of crops and other plants. For example, introduction of genes into chloroplast may lead to plants with increased viability in otherwise hostile environments and increased efficiency of photosynthesis. In addition, the expression of exogenous genes within the chloroplasts is believed to be significantly more efficient in chloroplasts relative the expression of exogenous genes introduced into the nucleus of the cell. Thus transfection of chloroplasts may allow for more effective biosynthesis strategies for commercial compounds.

Phylogenetically, mitochondria and chloroplasts resemble early bacteria As such, applicants recognized that bacterial viruses (e.g., bacteriophage lambda), could potentially be utilized to introduce DNA into these animal and plant organelles.

SUMMARY OF THE INVENTION

The present invention is directed to compositions, methods and systems for introducing nucleic acid sequences into an organelle of an intact eukaryotic cell. One aspect of the present invention provides nucleic acid constructs and methods for delivering nucleic acids to specific organelles using a receptor:ligand approach. Typically, the targeted organelle expresses a receptor that binds a nucleic acid or nucleic acid vector. Accordingly, the present invention discloses methods and compositions for transfecting eukaryotic cell organelles through the use of a vector, for example a viral vector, that comprises a receptor/docking protein. Suitable viral vectors and receptors include but are not limited to a bacterial viral vector such as bacteriophage lambda.

Another aspect of the invention provides a system comprising an intact viable cell that comprises one or more modified organelles and a recombinant vector. The modified organelles comprise one or more receptors localized on the surface of the organelle, and the recombinant vector is selected based on its ability to specifically bind to the receptor located on the modified organelle. Other aspects of the invention provide methods of correcting genetic defects, augmenting expression of specific nucleic acids, interfering with the expression of specific nucleic acids, restoring or augmenting organelle function, increasing biosynthesis of specific nucleic acids and their corresponding proteins using targeted delivery of nucleic acids to specific cellular organelles or compartments. Still other aspects of the present invention are directed to minimizing or reducing disease progression, alleviating symptoms, and adjusting cellular metabolism. Particular aspects are directed targeted delivery of nucleic acids to organelles containing the components for replication, transcription, or translation, or a combination thereof such as the mitochondrion or chloroplast.

BRIEF DESCRIPTION OF THE DRAWINGS

FIG. 1 shows a single organelle (e.g. a Rho mitochondria) (1) of a eukaryotic cell, including the inner (5) and outer (4) membranes, wherein the mitochondria contains a viral receptor (2) localized to organelle surface. A viral vector (6) comprising the desired recombinant DNA (3) is introduced into the cytosol of the cell using standard transfection techniques and the vector comes in contact with the receptor localized on the mitochondrial surface (2). The viral vector attaches to the receptor and the mitochondrial DNA is released into the interior of the mitochondria. The DNA is then replicated, transcribed, and its gene products translated by the mitochondrial machinery.

FIG. 2A represents complex IV activity and FIG. 2B represents complex I activity. The transfected mitochondria exhibit ETC activity indicating functional recovery of mtDNA gene products.

DETAILED DESCRIPTION OF THE INVENTION

Definitions

Figure 1:
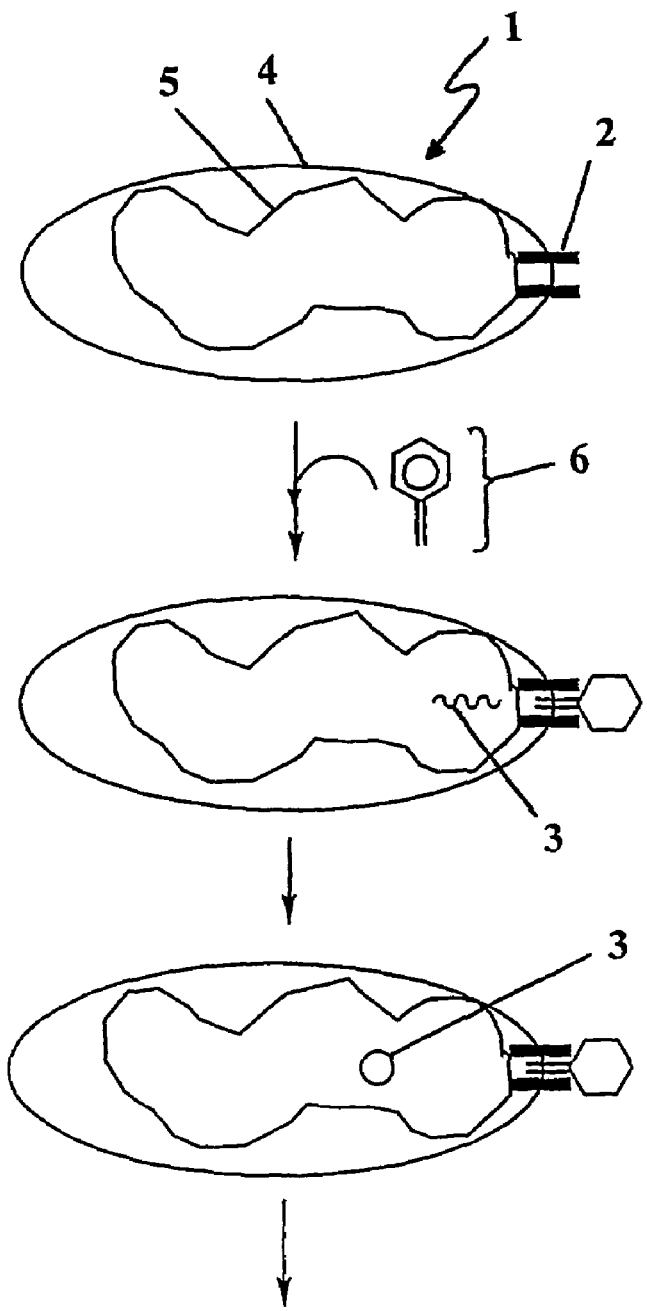
FIG. 1 is a schematic of the method using viral vectors to transfect an organelle of a eukaryotic cell.

In describing and claiming the invention, the following terminology will be used in accordance with the definitions set forth below.

As used herein, the term "purified" and like terms relate to the isolation of a molecule or compound in a form that is substantially free (at least 60% free, preferably 75% free, and most preferably 90% free) from other components normally associated with the molecule or compound in a native environment.

As used herein, the term "pharmaceutically acceptable carrier" encompasses any of the standard pharmaceutical carriers, such as a phosphate buffered saline solution, water and emulsions such as an oil/water or water/oil emulsion, and various types of wetting agents.

As used herein, the term "treating" includes alleviating the symptoms associated with a specific disorder or condition and/or preventing or eliminating said symptoms.

"Operably linked" refers to a juxtaposition wherein the components are configured so as to perform their usual function. For example, control sequences or promoters operably linked to a coding sequence are capable of effecting the expression of the coding sequence, and an organelle localization sequence operably linked to protein will direct the linked protein to be localized at the specific organelle.

As used herein, the term "exogenous DNA" or "exogenous nucleic acid sequence" refers to a nucleic acid sequence that was introduced into a cell or organelle from an external source. Typically the introduced exogenous sequence is a recombinant sequence.

As used herein, the term "transfection" refers to the introduction of a nucleic acid sequence into the interior of a membrane enclosed space of a living cell, including introduction of the nucleic acid sequence into the cytosol of a cell as well as the interior space of a mitochondria, nucleus or chloroplast. The nucleic acid may be in the form of naked DNA or RNA, associated with various proteins or the nucleic acid may be incorporated into a vector.

As used herein, the term "mitofection" refers to the introduction of a nucleic acid sequence into the interior of a mitochondria As used herein, the term "vector" is used in reference to a vehicle used to introduce a nucleic acid sequence into a cell. A viral vector is virus that has been modified to allow recombinant DNA sequences to be introduced into host cells or cell organelles.

As used herein, the term "organelle" refers to cellular membrane bound structures such as the chloroplast, mitochondrion, and nucleus. The term "organelle" includes natural and synthetic organelles.

As used herein, the term "non-nuclear organelle" refers to any cellular membrane bound structure present in a cell, except the nucleus.

The Invention

Cellular organelles have significant roles in the life cycle of cells and their hosts. For example, mitochondria and chloroplasts are the "powerhouses" of animal and plant cells. Because of their critical activity in maintaining cell life and bioenergetics, they play major roles in cell function and cell death. They possess their own unique genomes—which, until now, have remained un-amenable to manipulation. Embodiments of the present invention provide compositions and methods for the delivery of a polynucleotide to a specific organelle, for example to mitochondria and chloroplasts.

Organelles

Eukaryotic cells contain membrane bound structures called organelles. Organelles can have single or multiple membranes and exist in both plant and animal cells. Depending on the function of the organelle, the organelle can consist of specific components such as proteins and cofactors. Some organelles, such as mitochondria and chloroplasts, contain their own genome. Nucleic acids are replicated, transcribed, and translated within these organelles. Proteins are imported and metabolites are exported. Thus, there is an exchange of material across the membranes of organelles.

Exemplary organelles include the nucleus, mitochondrion, chloroplast, lysosome, peroxisome, Golgi, endoplasmic reticulum, and nucleolus. Synthetic organelles can be formed from lipids and can contain specific proteins within the lipid membranes. Additionally, the content of synthetic organelles can be manipulated to contain components for the translation of nucleic acids.

Mitochondria

Mitochondria contain the molecular machinery for the conversion of energy from the breakdown of glucose into adenosine triphosphate (ATP). The energy stored in the high energy phosphate bonds of ATP is then available to power cellular functions. Mitochondria are mostly protein, but some lipid, DNA and RNA are present. These generally spherical organelles have an outer membrane surrounding an inner membrane that folds (cristae) into a scaffolding for oxidative phosphorylation and electron transport enzymes. Most mitochondria have flat shelf-like cristae, but those in steroid secreting cells may have tubular cristae. The mitochondrial matrix contains the enzymes of the citric acid cycle, fatty acid oxidation and mitochondrial nucleic acids.

Mitochondiral DNA is double stranded and circular. Mitochondrial RNA comes in the three standard varieties; ribosomal, messenger and transfer, but each is specific to the mitochondria. Some protein synthesis occurs in the mitochondria on mitochondrial ribosomes that are different than cytoplasmic ribosomes. Other mitochondrial proteins are made on cytoplasmic ribosomes with a signal peptide that directs them to the mitochondria. The metabolic activity of the cell is related to the number of cristae and the number of mitochondria within a cell. Cells with high metabolic activity, such as heart muscle, have many well developed mitochondria New mitochondria are formed from preexisting mitochondria when they grow and divide.

The inner membranes of mitochondria contain a family of proteins of related sequence and structure that transport various metabolites across the membrane. Their amino acid sequences have a tripartite structure, made up of three related sequences about 100 amino acids in length. The repeats of one carrier are related to those present in the others and several characteristic sequence features are conserved throughout the family.

Chloroplasts

The chloroplast is a photosynthetic organelle in eukaryotes with a double surrounding membrane. The fluid inside the double-membrane is called the stroma. The chloroplast has a nucleoid region to house its circular, naked DNA. The stroma is also the site of the Calvin Cycle. The Calvin Cycle is the series of enzyme-catalyzed chemical reactions that produce carbohydrates and other compounds from carbon dioxide.

Within the stroma are tiny membrane sacs called thylakoids. The sacs are stacked in groups. Each group is called a granum. There are many grana in each chloroplast. The thylakoid membranes are the site of photosynthetic light reactions. The thylakoids have intrinsic and extrinsic proteins, some with special prosthetic groups, allowing for electrons to be moved from protein complex to protein complex. These proteins constitute an electron transport system sometimes known as the Z-scheme.

The prosthetic group for two critical membrane proteins (P680 and P700) is a chlorophyll a pigment molecule. These chlorophyll-binding proteins give the thylakoids an intense green color. The many thylakoids in a chloroplast give the chloroplast a green color. The many chloroplasts in a leaf mesophyll cell give that cell a green color. The many mesophyll cells in a leaf give the leaf a green color. The chlorophyll molecule absorbs light energy and an electron is boosted within the electron cloud-in a resonating chemical structure surrounding a magnesium ion. This excited electron is removed by the surrounding electron transport proteins in the membrane. The movement of these electrons, and accompanying protons, results ultimately in the trapping of energy in a phosphate bond in ATP.

The thylakoid is thus the location for light absorption and ATP synthesis. The stroma uses the ATP to store the trapped energy in carbon-carbon bonds of carbohydrates. Some chloroplasts show developing starch grains. These represent complex polymers of carbohydrates for long-term storage.

Given the importance of mitochondria in human disease, cell proliferation, cell death, and aging, embodiments of the present invention encompass the manipulation of the mitochondrial genome to supply the means by which known mitochondrial diseases (LHON, MELAS, etc.) and putative mitochondrial diseases (aging, Alzheimers, Parkinsons, and Diabetes) can be treated. Given the bioenergetic functions of chloroplasts, the ability to introduce exogenous genes may lead to plants with increased viability in otherwise hostile environments and increased efficiency of photosynthesis. Furthermore, the expression of exogenous genes within the chloroplasts is believed to be significantly more efficient in chloroplasts relative the expression of exogenous genes introduced into the nucleus of the cell. Thus, other embodiments are directed to the transfection of chloroplasts for more effective biosynthesis strategies for commercial compounds.

Prior to the present invention, no effective techniques existed to introduce exogenous nucleic acids, for example DNA, and the genes they encode into mitochondria or chloroplasts. Phylogenetically, mitochondria and chloroplasts resemble early bacteria. One embodiment of the present invention is directed to a system that utilizes viral vectors, and more preferably, bacterial viruses to transfect cell organelles including chloroplasts and mitochondria. This unique molecular approach to replace, augment, or otherwise modify the chloroplast and mitochondrial genome allows, for the first time, exploration of critical questions in chloroplast and mitochondrial genetics and the development of novel therapies for mitochondrial and chloroplast related diseases.

Modified Organelles

In accordance with the present invention one exemplary method for transfecting a cellular organelle, for example non-nuclear organelles such as the mitochondria and chloroplasts, comprises the steps of introducing into the cytosol of a eukaryotic cell a recombinant vector, for example a viral vector, wherein the vector specifically binds to a receptor uniquely located on the surface of the organelle to be transfected. The term non-nuclear organelle is intended to encompass all organelles other than the nucleus. It will be appreciated the target organelle can express a receptor or a ligand which causes a vector expressing a corresponding ligand or receptor to associate with the organelle. The receptor:ligand association of the organelle and vector can be ionic, non-covalent, covalent, reversible or irreversible. Exemplary receptor-ligand associations include but are not limited to protein-protein, protein-carbohydrate, protein-nucleic acid, nucleic acid-nucleic acid, protein-lipid, lipid-carbohydrate, antibody-antigen, or avidin-biotin. The receptor or ligand on the surface of the organelle or vector can be a protein, peptide, antibody, antibody fragment, lipid, carbohydrate, biotin, avidin, streptavidin, chemical group, or other ligand that causes specific association between the organelle and vector.

The specific interaction between the introduced vector and its target organelle can be accomplished by at least two methods. In one exemplary method a recombinant viral vector can be mutated so that it binds to an endogenously expressed surface protein located on the target organelle. Preferably, the endogenously expressed surface protein is one that is only expressed on the target organelle. In another method the target organelle is modified to incorporate an exogenous receptor protein to which a viral vector binds. Alternatively, a vector can be modified to specifically interact with a desired organelle.

In accordance with another embodiment of the invention a mutant lambda bacteriophage is used as a recombinant viral vector. Lambda phage binds to its bacterial receptor (the "lambda receptor" or lamB protein) via the fiber structure at the end of the tail. The tail fiber is composed of one protein subunit, the gpJ protein, which self-assembles in packaging bacteria or in vitro. Mutations in gpJ of lambda can alter the binding specificity of the lambda phage, thus allowing for the selection of mutant lambda that bind to proteins naturally associated with organelles of eukaryotic cells, and more particularly proteins associated with the surface of chloroplasts or mitochondria (see U.S. Pat. No. 5,736,388, the disclosure of which is expressly incorporated herein). Accordingly, in one embodiment a lambda bacteriophage vector is selected as a delivery vehicle wherein lambda bacteriophage specifically binds to an epitope present on the target organelle, for example an epitope that is only present on the target organelle. The epitope can be all or part of a protein, lipid, sugar group such as a carbohydrate or a combination thereof. In this embodiment the lambda vector is introduced into the cytosol of a cell, the vector binds to its receptor, and the nucleic acid present in the vector is introduced into the organelle. It will be appreciated by those skilled in the art that the target organelle can be transfected extracellularly or intracellularly. If the target organelle is transfected extracellularly, the transfected organelle can then be introduced to a cell using techniques known in the art such as fusion, electroporation, microinjection, ballistic bombardment, or liposomes.

One embodiment of the invention provides a cell having a modified organelle, wherein the modified organelle includes an exogenously introduced receptor that specifically binds a nucleic acid sequence or a vector containing a nucleic acid sequence, for example a viral receptor. An exogenous receptor means a receptor not naturally associated with the organelle or located on the organelle's surface. The receptor protein expressed on the organelle surface can be transcribed and/or translated within the organelle. Additionally, the receptor protein can undergo posttranslational modification within the organelle, if necessary, to facilitate the insertion of the receptor into the outer membrane of the organelle. In another embodiment, the receptor protein can be translated in the cytosol and delivered to the target organelle where all or part of the receptor is associated with the outer surface of the membrane. Associated with the outer surface of the membrane means that the receptor protein can be inserted into the organelle's outer membrane with the vector recognition site exposed on the outer surface or the receptor protein can be ionically, non-covalently, or covalently associated with the outer surface of the membrane such that the vector recognition site is exposed and capable of binding a desired vector. Delivery of proteins to specific organelles can be accomplished using targeting sequences, for example the targeting sequences in Table 1.

Nucleic acids including but not limited to polynucleotides, anti-sense nucleic acids, peptide nucleic acids, natural or synthetic nucleic acids, nucleic acids with chemically modified bases, RNA, DNA, RNA-DNA hybrids, enzymatic nucleic acids such as ribozymes and DNAzymes, native/endogenous genes and non-native/exogenous genes and fragments or combinations thereof, can be introduced into organelles of a host cell, in particular organelles that can transcribe and or translate nucleic acids into proteins such as mitochondria and chloroplasts. In one embodiment of the present invention, all or part of the mitochondrial or chloroplastic genome can be introduced into an organelle.

Another embodiment provides a method for transfecting eukaryotic cell organelles wherein the first step comprises providing a cell that contains a modified organelle, wherein the modified organelle comprises an exogenous receptor, such as the lambda receptor. This cell is then transfected with a recombinant vector, for example a viral vector, in a manner that introduces the vector into the cytosol of said cell as an intact functioning vector. The vector then binds to its specific receptor located on the target organelle and the recombinant DNA is introduced into the organelle.

A vector is introduced into the cytosol of a eukaryotic cell, in an intact functional form, through the use of standard techniques known to those skilled in the art. Such transfection procedures include but are not limited to microinjection, electroporation, calcium chloride permeabilization, polyethylene glycol permeabilization, protoplast fusion or cationic lipid permeabilization. In one embodiment a viral vector is introduced into the cell through the use of the Bioporter protein delivery system (Gene Therapy Systems, Inc. San Diego, Calif.).

In accordance with one embodiment a method is provided for introducing exogenous nucleic acid sequences into a mitochondrion of a mammalian cell. Any mitochondrial transfection technique should ensure that a nucleic acid crosses three membranes (the plasma membrane and the outer and inner mitochondrial membranes), addresses the high copy of mtDNA molecules, and utilizes a minimal, circular mitochondrial replicon. In one embodiment of the present invention a recombinant bacteriophage is used as a delivery vehicle for introducing nucleic acid sequences into an organelle, for example the mitochondrion.

In accordance with another embodiment a recombinant bacteriophage is used for mitochondrial transfection, and more preferably lambda bacteriophage is used to introduce exogenous nucleic acid sequences into mammalian cell mitochondria. This approach allows for direct manipulation of mtDNA and introduction of the circular genome at high-copy number, relying upon the properties of bacteriophage lambda to infect the cell's mitochondria. In particular, the 50 kilobase bacteriophage lambda genome can be engineered with large (>10 kilobase) inserts and packaged to form active lambda phage. In one embodiment, the only lambda sequences contained in the vector are the two cos sites (12 bp each) located at the 5' and 3' ends of a linear fragment to be packaged in a lambda particle, leaving up to about 50 kb available for a nucleic acid sequence of interest. The recombinant sequences may also include an origin of replication (usually ColE1) which allows replication in bacteria, and a gene coding for a selectable marker.

Since the minimal mitochondrial replicon is unknown, the complete human mitochondrial genome (SEQ ID NO: 8) or partial fragment thereof can be inserted into lambda, with 50 copies per active phage. In one embodiment this method is used to manipulate or replace mtDNA. In another embodiment the entire human mitochondrial genome can be replaced by introduced sequences. For example, Rho$^3$ cells can be first generated to remove endogenous mtDNA, followed by mitochondrial transfection, resulting in the entire mitochondrial genome of cells being replaced. Alternatively, mitochondria can be transfected without first proceeding with the generation of Rho$^0$ cells. In this case the introduced nucleic acid will be incorporated (recombined) with the existing endogenous mtDNA sequences resulting in the manipulation of the mtDNA sequences. Either method can be used to restore full functionality to damaged mitochondria.

In one embodiment, a lambda phage vector is used wherein the structural proteins of the bacteriophage have been modified to allow the bacteriophage to bind to a native surface protein located on the mitochondria surface. Preferably the surface protein is one that is unique to the organelle of interest, such as VDAC for mitochondria. Wild type lambda phage binds to its bacterial receptor (the lamB protein) via the fiber structure at the end of the tail. The tail fiber is composed of one protein subunit, the gpJ protein, and this protein can be modified to produce a bacteriophage that is capable of specifically interacting with eukaryotic transmembrane proteins (see U.S. Pat. No. 5,736,388, the disclosure of which is expressly incorporated herein).

In an alternative embodiment a lambda vector is utilized that retains its natural affinity for the lambda receptor (the lamB protein). Since native human mitochondria lack the bacteriophage lambda receptor or known homologous proteins (BLAST, E<10$^5$), the first step in this embodiment is to produce cells that contain mitochondria that express the lambda receptor on the surface of the mitochondria. To produce such cells, a cell is transfected with a nucleic acid (preferably DNA) construct comprising a sequence that encodes for a mitochondria localization sequence operably linked to the lambda receptor encoding sequence. Suitable mitochondria localization sequences are known to those skilled in the art (see Table 1) and include the mitochondrial localization signal of subunit VIII of human cytochrome oxidase, the yeast cytochrome c oxidase subunit IV presequence and the amino-terminal leader peptide of the rat ornithine-transcarbamylase. In one embodiment the introduced sequences are transiently expressed in the host cell. Alternatively the sequences can be inserted into the nuclear DNA of the host cell to produce a stably transformed cell that expresses the recombinant viral receptor. Upon expression of the recombinant receptor, the mitochondrial localization signal causes the viral receptor to be localized to the mitochondria. Subsequent transfection of this host cell with a suitable viral vector will target the vector to the mitochondria.

In accordance with one embodiment a eukaryotic host cell is provided that expresses the lambda receptor on the surface of the mitochondria. More particularly the host cell is a mammalian cell that comprises a recombinant nucleic acid construct, wherein the construct comprises a mitochondrial localization signal operably linked to the lambda receptor. When such a host cell is transfected with recombinant bacteriophage lambda, the lambda vector binds to its receptor expressed on the mitochondrial surface, the mitochondrial-lambda genome is introduced into the mitochondria, and is re-circularized, reproducing the intact circular mtDNA particle Nucleic acids encoding a receptor for a vector, for example a viral receptor for a viral vector, can be operatively linked to an organelle targeting sequence, for example amino acids used to import proteins into the mitochondria. This hybrid protein-nucleic acid can be used to target nucleic acids encoding a vector receptor to the organelle. Once inside the organelle, the nucleic acid encoding the vector receptor can be integrated into the genome of the organelle. Alternatively, the nucleic acid can remain episomal. Expression of the vector receptor nucleic acid can be controlled using controlling elements known/in the art such that expression is turned on or off by the presence or absence of an inducer or repressor substance.

In still another embodiment, nucleic acids encoding a vector receptor and an organelle targeting sequence can be introduced into a cell, for example a eukaryotic cell, and translated in the cytosol. The resulting protein contains a sequence of amino acids, typically less than about 30 amino acids, that targets the translation product to a specific organelle. The target organelle can internalize the translation product and express the vector receptor on the outer membrane of the organelle. The targeting sequence can be enzymatically cleaved if necessary such that the vector receptor is free to bind to its cognate vector.

In one embodiment, the cell expresses a recombinant DNA sequence comprising an organelle localization signal operably linked to a sequence encoding a specific bacterial viral receptor. In this embodiment, the target organelles are engineered to contain the natural receptor of the viral vector selected for transfecting the eukaryotic cell organelles. Thus, the use of such modified cells eliminates the need for viral vectors that have been modified to alter their receptor affinity. For example, if the viral vector is a lambda bacteriophage, then the target organelles are modified to express the lambda receptor on the surface of the organelle.

In accordance with this embodiment a transfection system is provided that comprises two components, the viral vector that delivers the nucleic acid of interest, for example RNA, DNA, or a combination thereof, and a nucleic acid construct (or cells comprising such a construct), wherein the construct comprises a nucleic acid sequence that encodes an organelle localization sequence operably linked to a receptor specific for the viral vector. The nucleic acid construct also optionally includes a suitable promoter for expressing the fusion protein as well as any other necessary regulatory elements for expressing the fusion protein. Such regulatory elements are well known to those skilled in the art and will vary based on the cell type to be transfected. One viral vector suitable for use with the present invention is bacteriophage lambda. When bacteriophage lambda is used as the transfection vector, the second component of the transfection system comprises a nucleic acid sequence encoding the lambda receptor (lamb) operably linked to the organelle localization sequence.

Cells that comprise organelles that express a desired receptor, for example a viral receptor, on their surface can be prepared using standard molecular biology techniques. In general, a host cell is transfected with a recombinant nucleic acid construct comprising a sequence that encodes an organelle localization signal operably linked to a sequence encoding the desired receptor, for example a viral receptor. The organelle localization sequence allows a protein that is linked to the localization sequence (i.e., a fusion protein) to be delivered to the target of the localization sequence. According to one embodiment of the present invention, the localization sequence is used to target a specific receptor to an organelle of choice, for example mitochondria or chloroplast, and thus provide a docking point for a subsequently introduced vector that binds to the receptor. The vector is introduced into the cytosol of the cell and then binds to the organelle expressing the receptor specific for the vector. The nucleic acid of interested within the vector is delivered into the target animal or plant organelle. The vector can be endocytosed or the nucleic acid sequence of interest can be injected into the organelle, for example when the vector is a viral vector such as bacteriaphage lambda.

Organelle localization signals are known to those skilled in the art, and any of those signals can be used to target the receptor protein or nucleic acid for expression on the target organelle. Localization sequences suitable for use in the present invention are described in Emanuelsson et al., Predicting Subcellular Localization of Proteins Based on Their N-terminal Amino Acid Sequence *Journal of Molecular Biology.* 300(4):1005-16, 2000 Jul. 21, and in Cline and Henry, Import and Routing of Nucleus-encoded Chloroplast Proteins. *Annual Review of Cell & Developmental Biology.* 12:1-26, 1996, the disclosures of which are incorporated herein. More particularly, a list of mitochondria localization signals for targeting linked proteins or nucleic acids to the outer membrane of the mitochondria is listed in TABLE 1. A list of chloroplast localization signals for targeting linked proteins or nucleic acids to the outer membrane of the chloroplasts is listed in TABLE 2. In one embodiment the mitochondria or chloroplast localization signal is operably linked to a bacterial virus receptor selected from the group consisting of OmpF, OmpC, PhoE and lamB.

TABLE 1

Localization Signals for Targeting to the Outer Mitochondrial membrane:

| Accession No. | PROTEIN |
|---|---|
| P19367 | HK1 hexokinase I |
| P21397 | MAOA amine oxidase (flavin-containing) A |
| P35557 | GCK hexokinase IV, pancreatic beta cell form |
| NP009295 | BZRP-S peripheral benzodiazepine receptor-related protein |
| AAH67831 | MTX2 metaxin 2 - human |
| AAD01798 | HTOM putative mitochondrial outer membrane protein import receptor (hTOM) - human |
| P10620 | GST12 glutathione transferase, microsomal |
| NP003366 | VDAC2 voltage-dependent anion channel 2 (outer mitochondrial membrane protein porin) |
| P35557 | GCK hexokinase IV, minor hepatic form |
| P00167 | CYB5 cytochrome b5, microsomal form |
| P00167 | CYB5 cytochrome b5, erythrocyte form |
| AAY45787 | BZRP peripheral benzodiazepine receptor |
| NP003479 | AKAP1 germ cell kinase anchor S-AKAP84 |
| NP003479 | AKAP84 A kinase anchor protein - human |
| NP001867 | CPT1A carnitine O-palmitoyltransferase I precursor |
| AB149509 | HK2 hexokinase II |
| P27338 | MAOB amine oxidase (flavin-containing) B |
| P33121 | FACL2 long-chain-fatty-acid--CoA ligase 2- human |
| P33121 | FACL1 long-chain-fatty-acid--CoA ligase 1 (palmitoyl-CoA ligase) |
| NP003365 | VDAC1 voltage-dependent anion channel 1 |
| CAI95086 | MTX1 metaxin 1 - human |
| NP006800 | HTOM34P Human putative outer mitochondrial membrane 34 kDa translocase hTOM34 - human |
| AAD14180 | VDAC4 voltage-dependent anion channel 4 (outer mitochondrial membrane protein porin) (272 nt) |
| P00387 | DIA1 cytochrome-b5 reductase |
| AAD49610 | VDAC3 voltage-dependent anion channel 3 (outer mitochondrial membrane protein porin) (273 nt) |

TABLE 1-continued

Localization Signals for Targeting to the Outer Mitochondrial membrane:

| Accession No. | PROTEIN |
|---|---|
| NP055580 | KIAA0016 Mitochondrial import receptor subunit TOM20 homolog (Mitochondrial 20 kd outer membrane protein) (Outer mitochondrial membrane receptor TOM20) (KIAA0016) - human |
| AAL53523 | TID1 tumorous imaginal discs homolog precursor (HTID-1) - human |

TABLE 2

Localization Signals for Targeting to the Outer Chloroplast membrane:

| Accession No. | PROTEIN |
|---|---|
| Q9XJ27 | Transit peptide domain of the apicoblast ribosomal protein S9 |
| P27456 | Pea glutathione reductase (GR) signal peptide |
| BAB91333 | NH$_2$-terminus of Cr-RSH encoding a putative guanosine 3',5'-bispyrophosphate (ppGpp) synthase-degradase |
| CAB42546 | 14-3-3 proteins |
| AAC64139 | Chloroplast signal recognition particle including cpSRP54, cpSRP43 subunits or a fragment thereof |
| AAC64109 | |
| AAD01509 | |
| PWSPG, FESP1, P00221, P05435, BAA37170, BAA37171, AAA81472 | Chloroplast transit peptides |
| Q43715 | AtOEP7, in particular the transmembrane domain (TMD) and its C-terminal neighboring seven-amino acid region (see Lee Y J, Plant Cell 2001 Oct; 13(10): 2175-90) |
| Q38814 | THI1 N-terminal chloroplastic transit peptide, in particular 4 to 27 residues |

The identification of the specific sequences necessary for translocation of a linked protein into a chloroplast or mitochondria can be determined using predictive software known to those skilled in the art.

Transfection of Plants

Techniques for plant transfection are known in the art. For example, *Agrobacterium tumefaciens* and *Agrobacterium rhizogenes* both have the ability to transfer portions of their DNA into the genomes of plants and can be used to transfect plant cells. The mechanism by which they transfer DNA is the same, however the differences in the resulting phenotypes are attributed to the presence of a Ti plasmid in Agrobacterium tumefaciens and the Ri plasmid in Agrobacterium rhizogenes. The Ti plasmid DNA induces host plants to grow tumourous masses whereas the Ri plasmid DNA leads to the abundant proliferation of roots. *Agrobacterium tumefacies* is capable of infecting almost any plant tissue whereas Agrobacterium rhizogenes can only infect roots.

The Ti plasmid of Agrobacterium is a large, circular double stranded DNA molecule (T-DNA) of approximately 200 kb, which exist as an autonomous replicating unit. The plasmids are maintained within the bacteria and only a specific region (T-region) approximately 20 kb can be transferred from the bacteria to the host. To accomplish this transfer the Ti plasmid contains a series of genes that code for its own replication, excision from the plasmid, transfer to the host cell, incorporation into the host genome and the induction of tumor formation Agrobacterium can detect and migrate towards injured plant cells through the detection of chemical signals leaking from the wounded plant. This detection process is referred to as chemotaxis. Agrobacterium can recognize plant compounds such as acetosyringone, sinapinic acid, coniferyl alcohol, caffeic acid and methylsyringic acid which induce the bacteria's virulence. To begin the infection process, Agrobacterium must bind itself to the host cell. This binding is achieved by a group of genes located within the bacterial chromosome. The bacteria can anchor at the site of injury, by the production of cellulose fibrils. The fibrils attach to the cell surface of the plant host and facilitate the clustering of other bacteria on the cell surface. It is believed that this clustering many help the successful transfer of T-DNA. Once bound to the host, the bacterium is free to begin the processing and transfer of the T-region. One embodiment of the present invention discloses transfecting a plant cell with Agrobacterium wherein the Agrobacterium has been modified to bind to a plant organelle, for example a chloroplast. Agrobacterium can be further modified to encode a nucleic acid of interest for expression in the organelle. Upon binding to the organelle, the Agrobacterium can deliver the target nucleic acid into the chloroplast.

To transfer the T-region of the Ti plasmid to the host cell organelle, the T-region must be processed such that it is excised from the plasmid and directed to the organelle. The T-region is excised from the Ti plasmid and directed into the host cell or organelle. Once properly packaged, the T-complex transfer is mediated by several proteins and is thought to be similar to bacterial conjugation. Once inside the plant cell or organelle, the T-complex is taken through the membrane.

Exemplary Cells and Cell Lines

In another embodiment, a nucleic acid encoding a vector receptor can be stably introduced into organelles of cells from a cell line. For example, a nucleic acid encoding a vector receptor operatively linked with an organelle targeting sequence can be used to transfect a eukaryotic cell line such that the nucleic acid sequence is stably integrated into the genome of a cell of the cell line. Alternatively, the nucleic acid encoding the vector receptor can be episomal. The cell line can be a transformed cell line that can be maintained indefinitely in cell culture, or the cell line can be a primary cell culture. Exemplary cell lines are those available from American Type Culture Collection including plant cell lines which are incorporated herein by reference. The nucleic acid can be replicated and transcribed within the nucleus of a cell of the transfected cell line. When translated in the cytosol, the protein is targeted to the organelle specific for the organelle targeting sequence contained within the protein. The target organelle can internalize the protein and express the vector receptor component on the outer membrane of the organelle. The targeting sequence can be enzymatically cleaved if necessary such that the vector receptor is free to bind to its cognate vector.

Any eukaryotic cell can be transfected to produce organelles that express a specific receptor, for example exogenous viral receptors, including primary cells as well as established cell lines. Suitable types of cells include but are not limited to undifferentiated or partially differentiated cells including stem cells, totipotent cells, pluripotent cells, embryonic stem cells, inner mass cells, adult stem cells, bone marrow cells, cells from umbilical cord blood, and cells derived from ectoderm, mesoderm, or endoderm. Suitable differentiated cells include somatic cells, neuronal cells, skeletal muscle, smooth muscle, pancreatic cells, liver cells, and cardiac cells. Suitable plant cells can be selected from monocots and dicots, and include corn, soybeans, legumes, grasses, and grains such as rice and wheat.

If the organelle to be targeted is a chloroplast, then the host cell can be selected from known eukaryotic photosynthetic cells. If the organelle to be transfected is the mitochondrion, than any eukaryotic cell can be used, including mammalian cells, for example human cells. The cells are transfected to either transiently or stably express the viral receptor gene. In one embodiment a DNA construct encoding a viral receptor is integrated into the nuclear genome of a cell to produce a stable transgenic cell line that comprises organelles that express the desired viral receptor.

Research Tools

In one embodiment, the present invention is used as a tool to investigate cellular consequences of mtDNA expression, the mechanisms of heteroplasmy, mtDNA replication and inheritance, as well as threshold effects. Mitochondrial mutant mice can be generated using this approach, allowing investigators to study mutations in mtDNA not found in nature. More particularly, mitofection can used to generate cells that contain mitochondria that have identical genotypes or varying degrees of heteroplasmy. To prepare homoplastic cells, $Rho^0$ cells (devoid of mtDNA) are first prepared using standard techniques. For example $Rho^0$ cells can be generated using ethidium bromide as described in Miller et al., J. Neurochem. 67:1897, 1996. These $Rho^0$ cells are maintained and propagated on pyruvate containing supportive media and then transfected with a functional mitochondria genome. After metabolic selection, by removing pyruvate from supportive media, only those cells that contain successfully transfected mitochondria will survive, thus generating a population of cells that all have identical mitochondria genomes.

Cell lines having varying degrees of heteroplasmy can then be generated in a controlled manner by fusing two or more homoplasmy cell lines to generate cybrids. Cybrids can be generated using any of the known technique for introducing organelles into a recipient cell, including but not limited to polyethylene glycol (PEG) mediated cell membrane fusion, cell membrane permeabilization, cell-cytoplast fusion, virus mediated membrane fusion, liposome mediated fusion, microinjection or other methods known in the art.

Transgenic Non-Human Animals

Figure 3:
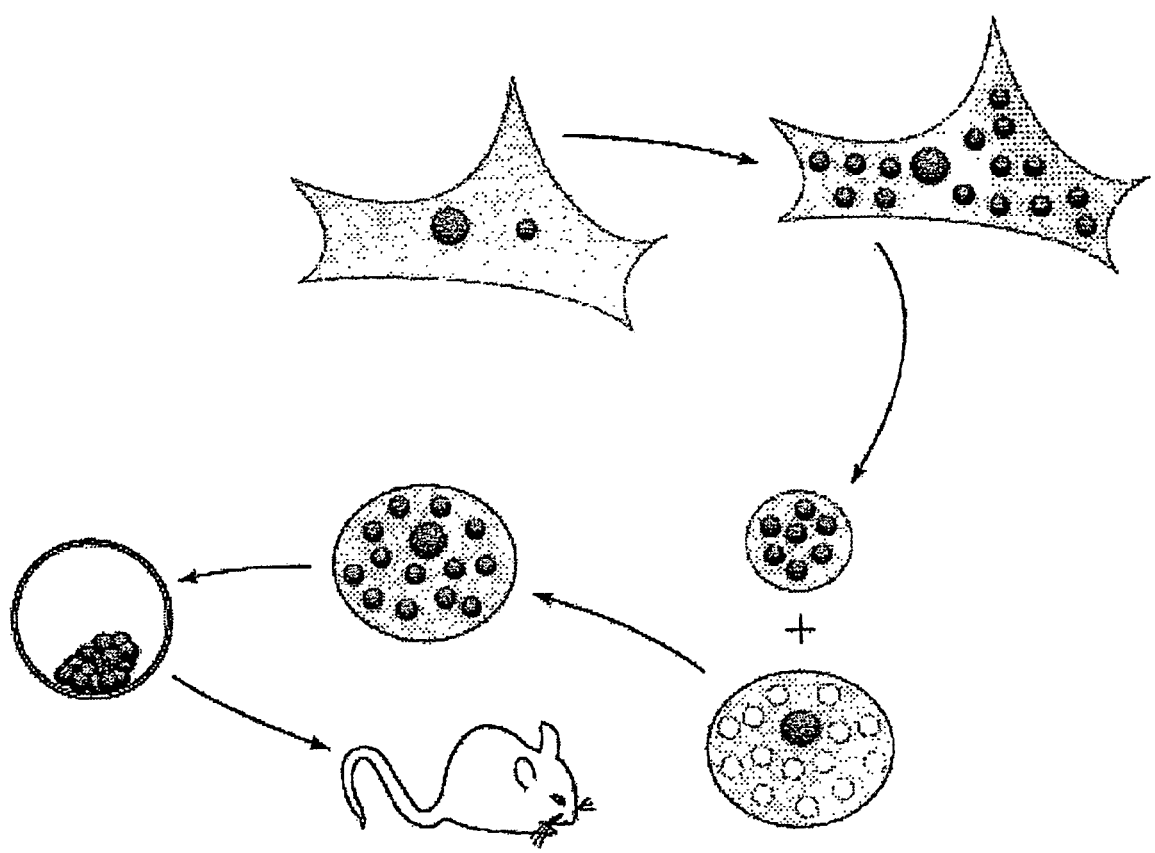
FIG. 3 is a schematic representation of the process for creating mice having transfected mitochondria. In the first step mitofected cells from embryonic stem cells (ES) Rhos are created with the DNA of interest followed by microinjection of the ES cells into the blastocyst. In one embodiment the mitofected mouse ES cells can be cultured for a predetermined length of time and then fused with another ES Rho cell (or other mitofected cell line) to form a cybrid, followed by microinjection of the resultant cybrid cells into the blastocyst. The resulting embryo is them implanted into surrogate mice to generate chimeric mice that comprise mitofected mitochondria.
Figure 4:
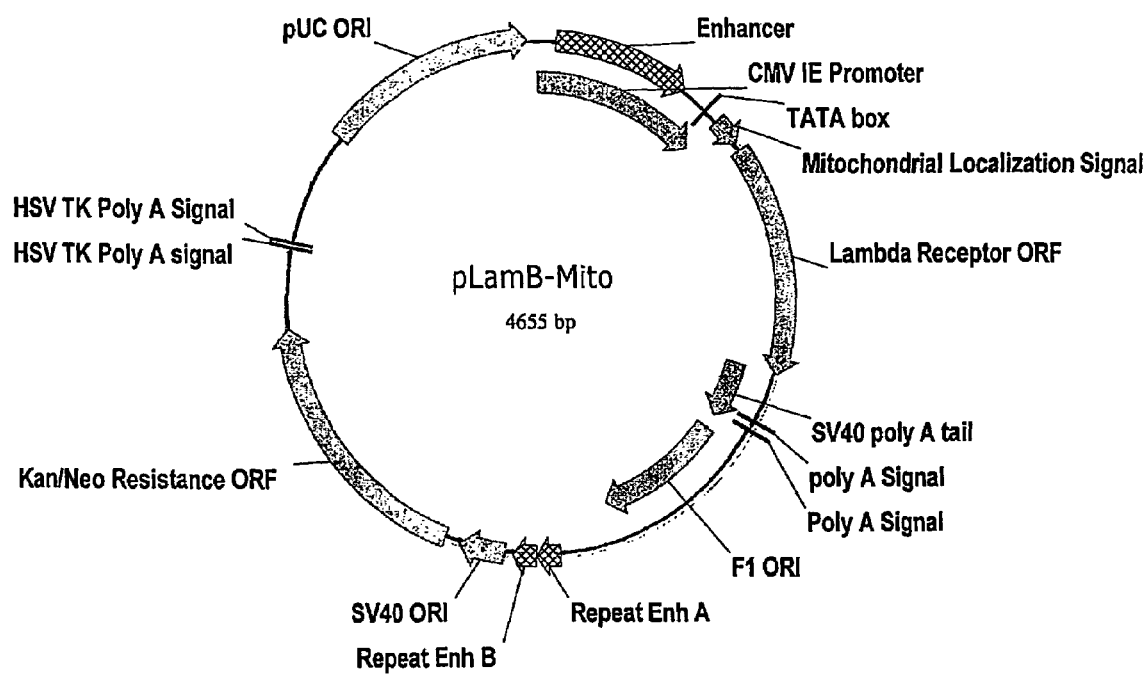
FIG. 4 is a schematic representation of the plasmid used to express a mitochondrial localization/lambda receptor fusion protein in a eukaryotic cell. In this embodiment the mitochondria localization signal used was from subunit VIII of human cytochrome oxidase (Accession no. NP_004065)
Figure 5:
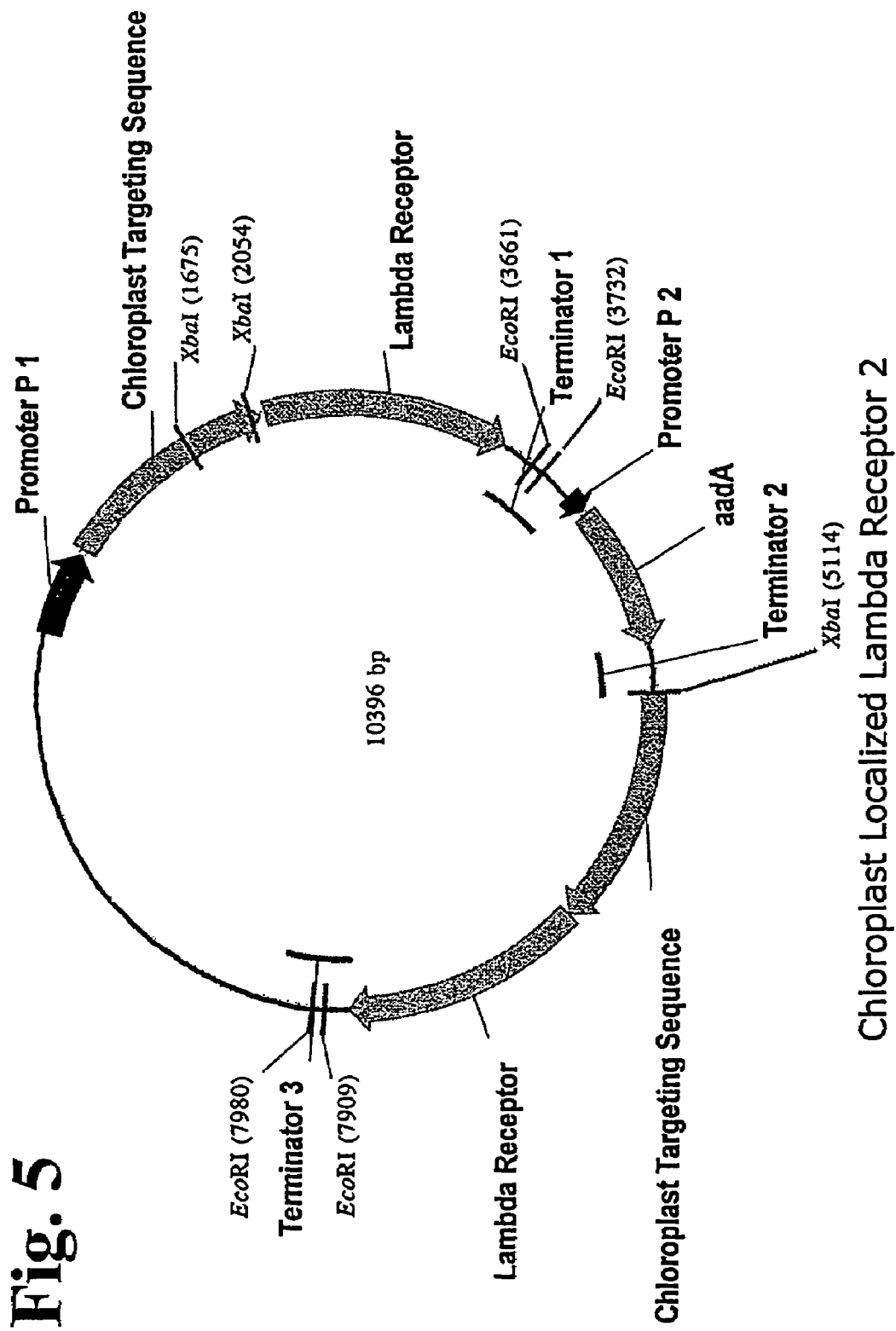
FIG. 5 is a schematic representation of the plasmid used to express a chloroplast localization/lambda receptor fusion protein in a eukaryotic cell. In this embodiment the chloroplast targeting sequence was derived from the chloroplast transformation vector pVSR326 (Accession no. AF527485).

The techniques described in the present invention can also be used to generated transgenic non-human animals. In particular, Zygote microinjection, nuclear transfer, blastomere electrofusion and blastocyst injection of embryonic stem (ES) cell cybrids have each provided feasible strategies for creating hetero- and homoplasmic mice containing mtDNA from mitofected cell lines (i.e. cells that containing transfected mitochondria). In one embodiment an embryonic stem (ES) cell is mitofected and injected into the blastocyst of a mammalian embryo as a means of generating chimeric mice. In another embodiment, embryonic stem (ES) cell cybrids (from mitofected cells and ES cell rhos, or from two separately mitofected cells) are first prepared, followed by blastocyst injection into embryos as shown in FIG. 3. The use of cells carrying specific mitofected mtDNA of interest allows the creation of transmitochondrial mice that are heteroplasmic or even homoplasmic for the mitofected DNA. In theory, this technique offers the prospect of transferring any mutant mtDNA that can be obtained from cultured mitofected cells into a whole organism model. Once combined with Mitofection, this could be used to create mouse models of human mtDNA disease.

Using lambda for mtDNA transfection ("Mitofection") will allow investigations into questions such as the effect of varying proportions of the 5000 bp "common deletion", which accumulates with aging, polymorphisms found in diabetes and neurodegenerative diseases, and dynamics of mtDNA complementation. There are also potential therapeutic uses of this approach. Targeted introduction of the normal mitochondrial genome offers treatment for both classic mtDNA-based diseases and diseases of aging such as neurodegenerative brain conditions and adult-onset diabetes, which have been associated with mtDNA-based mitochondrial dysfunction.

Kits

The present invention is also directed to a kit or pack that supplies the elements necessary to conduct transfection of eukaryotic organelles. In accordance with one embodiment a kit is provided comprising a nucleic acid, for example DNA, construct, that encodes an organelle localizing signal operably linked to a lambda receptor, and lambda packaging components for preparing a recombinant lambda vector. The kit may also include the lambda DNA sequences (the vector"arms") for inserting a DNA sequence of interest and subsequent use in generating a recombinant lambda phage vector. In one embodiment the DNA construct provided with the kit comprises a mitochondrial or chloroplast localization signal selected from those listed in Tables I and II, and more particularly in one embodiment the DNA construct comprises a sequence encoding the mitochondrial localization signal of subunit VIII of human cytochrome oxidase operably linked to the bacteriophage lambda receptor.

In accordance with one embodiment a kit is provided comprising cells that contain either a mitochondria or chloroplast organelle that expresses an exogenous receptor on the surface of the organelle. In a further embodiment a kit is provided that comprises packaging components for a viral vector, viral DNA for preparing recombinant constructs and cells that contain either a mitochondria or chloroplast organelle that expresses a receptor on the surface of the organelle that is capable of binding to the viral vector prepared using the kit. In one embodiment the kit is provided with lambda bacteriophage packaging extract, lambda DNA, and cells that comprise mitochondria or chloroplasts that express the lambda receptor on their outer membrane. More particularly, in one embodiment the cells provided with the kits of the present invention have been stably transformed with a DNA construct comprising an organelle localizing signal operably linked to a lambda receptor. The individual components of the kits can be packaged in a variety of containers, e.g., vials, tubes, microtiter well plates, bottles, and the like. Other reagents can be included in separate containers and provided with the kit; e.g., positive control samples, negative control samples, buffers, cell culture media, etc. Preferably, the kits will also include instructions for use.

Organelle Related Diseases or Syndromes

Organelle dysfunction can cause disease in a host, for example a human host or a plant host. In particular, problems with mitochondria or chloroplasts can result in disease. Mitochondrial diseases result from failures of the mitochondria, specialized compartments present in every cell of the body except red blood cells. Cell injury and even cell death are result from mitochondrial failure. If this process is repeated throughout the body, whole systems begin to fail, and the life of the person in whom this is happening is severely compromised. The disease can be in children, for example individuals less that 18 years of age, typically less than 12 years of age, or adults, for example individuals 18 years of age or more. Thus, embodiments of the present invention are directed to treating a host diagnosed with an organelle related disease, in particular a mitochondrial disease, by transfecting a host cell organelle, for example a mitochondrion, to express a receptor and introducing a vector into the host cell wherein the vector specifically binds to the receptor and wherein the vector comprises a nucleic acid encoding mitochondrial protein or peptide. The present invention encompasses manipulating, augmenting or replacing portions of the mammalian cell mitochondrial genome to treat diseases caused by mitochondrial genetic defects or abnormalities.

Exemplary mitochondrial diseases include but are not limited to: Alpers Disease; Barth syndrome; β-oxidation defects; carnitine-acyl-camitine deficiency; camitine deficiency; coenzyme Q10 deficiency; Complex I deficiency; Complex II deficiency; Complex III deficiency; Complex IV deficiency; Complex V deficiency; cytochrome c oxidase (COX) deficiency; Chronic Progressive External Ophthalmoplegia Syndrome (CPEO); CPT I Deficiency; CPT II deficiency; Glutaric Aciduria Type II; lactic acidosis; Long-Chain Acyl-CoA Dehydrongenase Deficiency (LCAD); LCHAD; mitochondrial cytopathy; mitochondrial DNA depletion; mitochondrial encephalopathy; mitochondrial myopathy; Mitochondrial Encephalomyopathy with Lactic Acidosis and Strokelike episodes (MELAS); Myoclonus Epilepsy with Ragged Red Fibers (MERRF); Maternally Inherited Leigh's Syndrome (MILS); Myogastrointestinal encephalomyopathy (MNGIE); Neuropathy, ataxia and retinitis pigmentosa (NARP); Leber's Hereditary Optic Neuropathy (LHON); Progressive external ophthalmoplegia (PEO); Pearson syndrome; Kearns-Sayre syndrome (KSS); Leigh's syndrome; intermittent dysautonomia; pyruvate carboxylase deficiency; pyruvate dehydrogenase deficiency; respiratory chain mutations and deletions; Short-Chain Acyl-CoA Dehydrogenase Deficiency (SCAD); SCHAD; and Very Long-Chain Acyl-CoA Dehydrongenase Deficiency (VLCAD).

Some mitochondrial diseases are a result of problems in the respiratory chain in the mitochondria. The respiratory chain consists of four large protein complexes: I, II, III and IV (cytochrome c oxidase, or COX), ATP synthase, and two small molecules that ferry around electrons, coenzyme Q10 and cytochrome c. The respiratory chain is the final step in the energy-making process in the mitochondrion where most of the ATP is generated. Mitochondrial encephalomyopathies that can be caused by deficiencies in one or more of the specific respiratory chain complexes include MELAS, MERFF, Leigh's syndrome, KSS, Pearson, PEO, NARP, MILS and MNGIE.

The mitochondrial respiratory chain is made up of proteins that come from both nuclear and mtDNA. Although only 13 of roughly 100 respiratory chain proteins come from the mtDNA, these 13 proteins contribute to every part of the respiratory chain except complex II, and 24 other mitochondrial genes are required just to manufacture those 13 proteins. Thus, a defect in either a nuclear gene or one of the 37 mitochondrial genes can cause the respiratory chain to break down. It will be appreciated that the scope of the present invention includes transfecting mitochondria with at least one or part of one gene involved in mitochondrial function, in particular at least one or part of the 37 mitochondrial genes to restore or increase the function of the respiratory chain. Any or part of a mitochondrial genome, for example human mitochondrial genome SEQ ID NO: 8, may be introduced into a host mitochondrion using the methods described herein.

Diseases of the mitochondria appear to cause the most damage to cells of the brain, heart, liver, skeletal muscles, kidney and the endocrine and respiratory systems. Thus, transfection of mitochondria in these cells and tissues with specific nucleic acids is within the scope of the present invention, in particular transfection of mitochondria with nucleic acids encoding mitochondrial-encoded proteins rather than nuclear-encoded proteins. It will be appreciated that the mitochondria can be transfected to express any protein whether naturally present in the mitochondrion or not or naturally encoded by mtDNA or nuclear DNA. Depending on which cells are affected, symptoms may include loss of motor control, muscle weakness and pain, gastro-intestinal disorders and swallowing difficulties, poor growth, cardiac disease, liver disease, diabetes, respiratory complications, seizures, visual/hearing problems, lactic acidosis, developmental delays and susceptibility to infection.

Exemplary mtDNA mutations that can be addressed by the present invention include but are not limited to: $tRNA^{leu}$-A3243G, A3251G, A3303G, T3250C T3271C and T3394C; $tRNA^{Lys}$-A8344G, G11778A, G8363A, T8356C; ND1-G3460A; ND4-A10750G, G14459A; ND6-T14484A; 12S rRNA-A1555G; MTTS2-C12258A; ATPase 6-T8993G, T8993C; $tRNA^{Ser}$(UCN)-T7511C; 11778 and 14484, LHON mutations as well as mutations or deletions in ND2, ND3, ND5, cytochrome b, cytochrome oxidase I-III, and ATPase 8.

One embodiment of the present invention provides a method for restoring or increasing respiratory chain function in host cell including transfecting a mitochondrion in the host cell to express a receptor on the outer surface of the mitochondrion; and introducing a vector into the host cell, wherein the vector specifically binds to the receptor on the outer surface of the mitochondrion and comprises a nucleic acid that encodes a respiratory chain protein or peptide. The nucleic acid of the vector can be injected or otherwise delivered into the interior of the mitochondria when the vector binds the receptor, for example when the vector is bacteriaphage lambda and the receptor is a bacteriaphage lambda receptor.

Another embodiment of the present invention provides a method for restoring or increasing cytochrome oxidase activity in a host including transfecting mitochondria in a cell, for example a skeletal muscle cell, of a host to express a receptor, and introducing a vector that specifically binds to the receptor, wherein the vector comprises a nucleic acid that encodes cytochrome oxidase or a functional component thereof. A functional component means a part or fragment of the protein or protein complex or subunit that performs a biological function independently or in combination with another protein, fragment, or subunit.

Still another embodiment of the present invention provides a method of increasing or restoring β-oxidation in a host including obtaining cells from the host, transfecting an organelle in the cells from the host to express a receptor, introducing a vector comprising a nucleic acid encoding proteins involved in β-oxidation spiral and carnitine transport, wherein the vector specifically binds to the receptor expressed on the organelle; and introducing the transfected cells of the host back into the host.

Other embodiments of the invention are directed to methods of restoring mitochondrial function lost or decreased as a result of point mutations or deletions. For example, KSS, PEO and Pearson, are three diseases that result from a type of mtDNA mutation called a deletion (specific portions of the DNA are missing) or mtDNA depletion (a general shortage of mtDNA). Thus, cells from hosts diagnosed with KSS, PEO, Pearson or similar disease can have their mitochondria transfected to express a receptor on the outer surface. A vector comprising a nucleic acid that corresponds to the deletion in the mtDNA causing the diseased state can be introduced into the cells containing the transfected mitochondria. The vector will bind the receptor and deliver the nucleic acid into the interior of the mitochondria where the nucleic acid is expressed. The expression product can then incorporate into the mitochondria and increase or restore mitochondrial function. The transfected cells can be reintroduced in the host. It will be appreciated that the host's cells or other cells can be transfected as described herein and introduced into a host having a dysfunctional organelles, in particular mitochondria.

It will be appreciated by those skilled in the art that the present invention encompasses delivering either separately or in combination nucleic acids to the mitochondria that are naturally encoded by mtDNA or nuclear DNA.

The present invention also contemplates alleviating the symptoms of mitochondrial diseases by creating cells having transfected and non-transfected mitochondria. Alternatively, all of the mitochondria in a cell can be transfected or replaced.

One embodiment provides a method for compensating for a mtDNA mutation in a host, the method including identifying a host having a mtDNA mutation, obtaining a cell comprising said mtDNA mutation from said host, transfecting a mitochondrion of the host cell to express a receptor, introducing a vector that specifically binds to the receptor into the host cell, wherein the vector comprises a nucleic acid that encodes a functional product corresponding to the mtDNA mutation, introducing said transfected cell into the host. A nucleic acid that encodes a fractional product corresponding to the mtDNA mutation means a sequence that produces a protein without the corresponding mutation. For example, if a host cell has an ND4-A10750G mutation, the transfected nucleic acid would encode a wildtype product for the ND4 gene. The transfected cells can be introduced into the host, for example, intravenously.

EXAMPLE 1

Mitochondrial Localization of the Lambda Receptor in Mammalian Cells

Lambda receptor cDNA was PCR amplified from *E. coli* K-12. *E. coli* K-12 (ATCC) genomic DNA was PCR amplified using the Clontech HotStart System with the following primers: ATG ATG TTA CTC CTG CGC AAA C (SEQ ID NO: 1) and TTA CCA CCA GAT TTC CAT CAG GG (SEQ ID NO: 2). The cDNA was TA-cloned into pIND/Topo (Invitrogen). The resulting plasmid (pIND-LamB) was digested with BamHI and AgeI (NEB). pDsRed1-Mito (Clontech) was digested with BamHI and AgeI, and the 1.3 kb lambda receptor fragment was inserted downstream of the mitochondrial localization signal of subunit VIII of human cytochrome oxidase. DH5a cells were transformed and the resultant pMLS-LambdaR plasmid was isolated and transfected into Rho cells.

To test for mitochondrial localization of the lambda receptor, human SH-SY5Y neuroblastoma $Rho^0$ cells devoid of mtDNA or ETC activity were transfected with the mitochondrially localized lambda receptor plasmid (pMLS-LambdaR). With confocal microscopy we noted red fluorescence in the usual mitochondrial punctate/perinuclear distribution. Since the lambda receptor-RFP fusion protein may sterically hinder proper lambda receptor function, the RFP cDNA was excised from pMLS-LambdaR for future experiments.

EXAMPLE 2

Transfection of Mitochondria and Expression of a Recombinant Gene Construct

The mitochondrial genome of control SH-SY5Y was PCR amplified around the region between the putative mitochondrial transcription terminator (MTTER) site and the tRNA for leucine. MtDNA was PCR amplified with EXPAND Long Template (Roche) using the following primers: ACA TAC CCA TGG CCA ACC TCC TAC TCC TCA (SEQ ID NO: 3) and CCT TTT CTT CTC CTT AAC TTG GAG ACT GAC (SEQ ID NO: 4). The following cycling parameters were used to generate the 16.6 kb product: 92° C. for 2 minutes, ten cycles of 92° C. for 30 sec, annealing at 58 ° C for 1 min, and 12 minutes of extension at 68 ° C. This was followed by 25 cycles of the previous ten cycles with a 20 sec step added to the extension time. The PCR product was ligated to NotI polylinkers and digested with NotI for insertion of EGFP (the mtDNA/EGFP/BamHI construct). Alternatively, the PCR product was ligated to BamHI polylinkers and digested with BamHI for ligation to the lambda vectors without containing the EGFP (the mtDNA/BamHI construct). Supercos-1 and Lambda Fix II (Stratagene) were prepared following manufacturer's instructions. The mtDNA/BamHI or mtDNA/EGFP/BamHI constructs were ligated to Supercos-1 and Lambda Fix II. The completed constructs were packaged into Lambda Packaging Extract (Stratagene).

To establish proof of principle, GFP was incorporated as a reporter gene. Since mitochondria possess a unique translation code, the GFP reporter gene was mutagenized to prevent translation except by the mitochondrial translation apparatus. Site-directed mutagenesis (Clontech) was carried out at nucleotide position 270, changing an A to G. The subsequent codon was changed from AGA to AGG. PEGFP from Clontech was mutagenized using the Clontech protocol in mutS-$E.$ $coli.$ Primers used were: Mutagenesis Primer Sequence: CTG CCC GTG CCC TGA CCC ACC CTC GTG ACC (SEQ ID NO: 5). Selection Primer1 Sequence: GAG CTC AAG CTT CGA ATC CTG CAG TCG ACG (SEQ ID NO: 6). Selection Primer2 Sequence: TTT GGA GGT CTA GGC TTT TGC AAA GAT CGA (SEQ ID NO: 7). In the mitochondrial translation code, the AGG remains a tryptophan; whereas in the nuclear translation code AGG is read as a stop codon. This strategy prevents completion of GFP translation outside of mitochondria by yielding a curtailed (70 aa long) non-fluorescing gene product.

The mito-GFP was ligated to the upstream MTTER. The mito-genome-GFP construct was then ligated to SuperCos-1 (Stratagene) flanking the T7 and T4 bacteriophage promoters and packaged to produce active lambda phage using commercially available lambda packaging extracts (Stratagene).

Using the Bioporter protein delivery system (Gene Therapy Systems), the bacteriophage was introduced into SH-SY5Y Rho$^0$ cells transiently expressing (24 hours post-transfection) the pMLS-LambdaR lambda phage receptor. Within the cytosol, the active lambda phage carrying the human mitochondrial genome and GFP was allowed to introduce its genome containing the mitochondrial construct. Since mitochondria possess a circular genome, the lambda phage was especially useful because of its ability to re-circularize its genomic DNA due to its cohesive ends (cos sites).

After metabolic selection by removing pyruvate from supportive media, which will cause normal Rho$^0$ cells to die, GFP reporter activity was observed in a punctate/perinuclear distribution. Control cells transfected with pMLS-LambdaR and packaging extract, showed no GFP fluorescence. Rho$^0$ cells possessing no lambda receptor but transfected with the active mito-lambda phage also showed no GFP fluorescence, suggesting the necessity of the expression of the lambda phage receptor for proper mitochondrial targeting.

To establish GFP co-localization with mitochondria, a fluorescent dye (Mito Tracker Red) preferentially taken up by mitochondria in a membrane potential dependent manner was utilized. Cells expressing pMLS-LambdaR and transfected with SuperCos-1/mtDNA/GFP cosmid showed colocalization of GFP with MitoTracker Red. Using a GFP antibody (Molecular Probes), Western blot analysis comparing a mitochondrial isolate with cytoplasmic and nuclear fractions revealed that mitochondrial fractions contain GFP immunostaining.

Since Rho$^0$ cells lack mtDNA gene products, they do not have functioning ETC complex I or IV and cannot consume oxygen or maintain normal mitochondrial membrane potentials. Following insertion of the mitochondrial genome into Rho$^0$ cells, the return of these bioenergetic activities would constitute evidence of expression and functional incorporation of mtDNA gene products.

The success of transfection was first assessed by demonstrating the presence of full-length mtDNA via PCR amplification on DNA isolates from transfected and control Rho$^0$ cells; a 16.5 kb PCR product was observed from transfected cells and none from controls. Furthermore, transfected cells showed mtDNA synthesis based on mitochondrial incorporation of bromo deoxyuridine (BrdU) staining that colocalized with GFP.

Since mtDNA replication requires the presence of primer mRNA, suggesting intact mtDNA transcription, mtDNA ETC gene products were searched for by Western blot. Positive bands for the mtDNA-encoded subunit I of Complex IV were detected in transfected cells and native SY5Y's, whereas no signals were observed in either transfectant controls or Rho$^0$ cells.

Figure 2A:
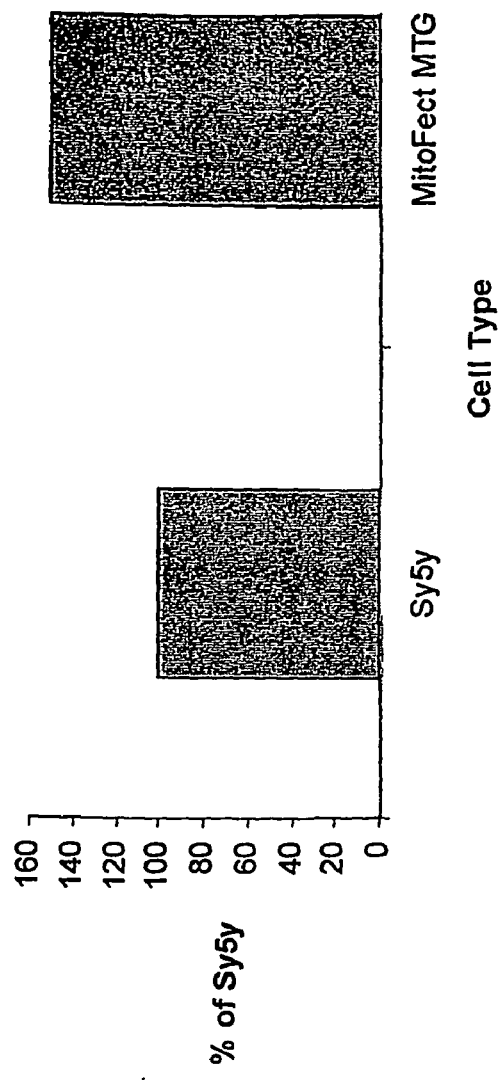
FIGS. 2A and 2B are a bar graphs representing the restoration of complex I and complex IV activities following transfection of SH-SY5Y Rho$^0$ cells with pMLS-LambdaR followed by SuperCos-1/mtDNA cosmid.
Figure 2B:
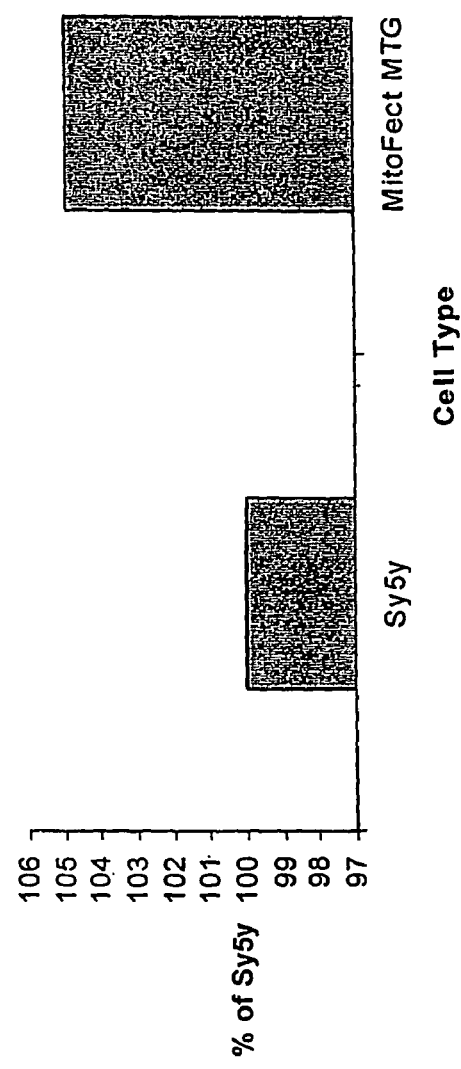

The transfected mtDNA-encoded gene products could be successfully incorporated into functioning ETC complexes as determined by assaying activities of Complex I and Complex IV. Complex I and IV activities in the cells exceeded by 50% that of native SY5Y's (see FIG. 2)—pointing to an increased rate of oxidative phosphorylation possibly due to the construct carrying the T7 and T4 bacteriophage promoters in addition to the heavy and light chain promoters of mtDNA.

Having shown that the transfected cells demonstrated intact Complex I and IV activities, oxygen polarography was then used to demonstrate ETC inhibitor-sensitive oxygen uptake. The mtDNA-transfected Rho$^0$ cells consumed oxygen at a rate comparable to control SH-SY5Y and reduce oxygen in an ETC dependant manner. Oxygen uptake by the mtDNA-transfected cells was sensitive to rotenone (an inhibitor of Complex I), KCN (an inhibitor of Complex IV) and was increased by the ETC uncoupler CCCP. No basal or CCCP-induced oxygen consumption was noted in the transfection control or Rho$^0$ cells.

Having demonstrated the successful introduction of full-length mtDNA, mtDNA-encoded proteins, and an intact electron transport chain and oxygen consumption, the cells were investigated for evidence of coupling of ETC activity to proton pumping, which normally accounts for the majority of the mitochondrial membrane potential ($DY_M$). The potential-sensitive dye JC-1 was used to estimate relative $DY_M$ in mtDNA-transfected cells lacking the GFP reporter but containing full-length mtDNA. An increase was observed in redfluorescing J-aggregate compared to transfection control, Rho⁰ and native SH-SY5Y. This demonstrated that ETC activity and oxygen consumption in the mtDNA-transfected cells allowed the return of $DY_M$ and provided evidence for functional coupling of newly expressed ETC complexes.

In summary, bacteriophage lambda was utilized containing the complete human mitochondrial genome to restore electron transport chain (ETC) activity in cells completely devoid of mtDNA (Rho⁰ cells). The reappearance of mtDNA, mtDNA-encoded ETC proteins, ETC function, mitochondrial membrane potential and ETC inhibitor-sensitive oxygen consumption was observed.

EXAMPLE 3

Rescue of a Mitochondrial Defect

The lambda bacteriophage-based mtDNA transfection strategy can also be used to rescue cell lines carrying mtDNA's from patients with mitochondrial diseases or mtDNA's mutated in vitro. For example, Leber's Hereditary Optic Neuropathy (LHON) is a disorder caused by mutations in mtDNA. The mutation in the NADH dehydrogenase subunit 4 gene is a G→ A transition at nt11778. This removes a restriction site for SfaN1. Therefore the presence of this mitochondrial defect can be detected by restricting the cells DNA with SfaN1 and observing the resulting fragments by gel electrophoresis. LHON cybrid cell lines were generated from a patient with Leber's Hereditary Optic Neuropathy (LHON), and these cells contained only the mutant mtDNA. Using the transfection strategy of the present invention, wild-type SH-SY5Y mtDNA was introduced into the LHON cybrids. These LHON-mtDNA transfectants demonstrated delivery of wild-type mtDNA.

Detection of the mutant and wild type NADH dehydrogenase sequences was conducted using PCR amplification and restriction endonuclease analysis. In particular, a 450 nucleotide amplicon encompassing this region was PCR amplified from the LHON cybrids, LHON cybrids mitofected with the wild-type genome, and from normal SY5Y cells. The amplicon was digested with SfaN1 (digestion into two fragments indicates a wild-type genome whereas no digestion indicates the LHON genotype). No digestion was observed in the LHON cybrids, however digestion was observed in the LHON cybrids mitofected with the wild-type genome and the SY5Y cells. Furthermore, quantative PCR post-transfection showed an increase of wild-type mtDNA over that of mutant mtDNA.

Therefore homoplasmic mitochondrial mutant cells were successfully rescued with wild-type mtDNA. These results are consistent with previous studies showing that rho⁰ cells contain normal levels of mtDNA polymerase and can engage in mtDNA transcription if provided with mtDNA template. This unique molecular approach allows efficient incorporation of mtDNA into mitochondria of cells and does not depend on mechanical processes. Such a technique allows for the first time, one to replace or augment the mitochondrial genome and thus explore critical questions in. mitochondrial genetics as well as develop novel therapies for mitochondrial diseases.

The invention claimed is:

1. An isolated nucleic acid comprising a sequence encoding a mitochondrial localization signal from subunit VIII of human cytochrome oxidase operably linked to a sequence encoding a viral receptor, wherein the viral receptor is expressed on an outer mitochondrial membrane after the nucleic acid has been transfected into a eukaryotic cell.

2. The nucleic acid of claim 1 wherein the viral receptor is selected from the group consisting of OmpF, OmpC, PhoE and lamB.

3. The nucleic acid of claim 2 wherein the viral receptor is lamB.

4. An isolated eukaryotic cell comprising the nucleic acid of claim 1.

* * * * *

SEQUENCE LISTING

```
<160> NUMBER OF SEQ ID NOS: 8

<210> SEQ ID NO 1
<211> LENGTH: 22
<212> TYPE: DNA
<213> ORGANISM: Artificial Sequence
<220> FEATURE:
<223> OTHER INFORMATION: lambda receptor PCR primer
<220> FEATURE:
<221> NAME/KEY: primer_bind
<222> LOCATION: (1)..(22)
<223> OTHER INFORMATION:

<400> SEQUENCE: 1
atgatgttac tcctgcgcaa ac                                              22

<210> SEQ ID NO 2
<211> LENGTH: 23
<212> TYPE: DNA
<213> ORGANISM: Artificial
<220> FEATURE:
<223> OTHER INFORMATION: lambda receptor PCR primer
<220> FEATURE:
<221> NAME/KEY: primer_bind
<222> LOCATION: (1)..(23)
<223> OTHER INFORMATION:

<400> SEQUENCE: 2
ttaccaccag atttccatca ggg                                             23

<210> SEQ ID NO 3
<211> LENGTH: 30
<212> TYPE: DNA
```

```
<213> ORGANISM: Artificial
<220> FEATURE:
<223> OTHER INFORMATION: Mitochondria PCR primer
<220> FEATURE:
<221> NAME/KEY: primer_bind
<222> LOCATION: (1)..(30)
<223> OTHER INFORMATION:

<400> SEQUENCE: 3
acatacccat ggccaacctc ctactcctca                              30

<210> SEQ ID NO 4
<211> LENGTH: 30
<212> TYPE: DNA
<213> ORGANISM: Artificial
<220> FEATURE:
<223> OTHER INFORMATION: Mitochondria PCR primer
<220> FEATURE:
<221> NAME/KEY: primer_bind
<222> LOCATION: (1)..(30)
<223> OTHER INFORMATION:

<400> SEQUENCE: 4 cctttcttc tccttaactt ggagactgac                               30

<210> SEQ ID NO 5
<211> LENGTH: 30
<212> TYPE: DNA
<213> ORGANISM: Artificial
<220> FEATURE:
<223> OTHER INFORMATION: GFP reporter mutagenesis PCR primer
<220> FEATURE:
<221> NAME/KEY: primer_bind
<222> LOCATION: (1)..(30)
<223> OTHER INFORMATION: GFP reporter mutagenesis PCR primer

<400> SEQUENCE: 5
ctgcccgtgc cctgacccac cctcgtgacc                              30

<210> SEQ ID NO 6
<211> LENGTH: 30
<212> TYPE: DNA
<213> ORGANISM: Artificial
<220> FEATURE:
<223> OTHER INFORMATION: GFP reporter PCR primer
<220> FEATURE:
<221> NAME/KEY: primer_bind
<222> LOCATION: (1)..(30)
<223> OTHER INFORMATION:

<400> SEQUENCE: 6
gagctcaagc ttcgaatcct gcagtcgacg                              30

<210> SEQ ID NO 7
<211> LENGTH: 30
<212> TYPE: DNA
<213> ORGANISM: Artificial
<220> FEATURE:
<223> OTHER INFORMATION: GFP reporter mutagenesis PCR primer
<220> FEATURE:
<221> NAME/KEY: primer_bind
<222> LOCATION: (1)..(30)
<223> OTHER INFORMATION:

<400> SEQUENCE: 7
tttggaggtc taggcttttg caaagatcga                              30

<210> SEQ ID NO 8
<211> LENGTH: 16569
```

```
<212> TYPE: DNA
<213> ORGANISM: Homo sapiens

<400> SEQUENCE: 8
gatcacaggt ctatcaccct attaaccact cacgggagct ctccatgcat ttggtatttt      60
cgtctggggg gtatgcacgc gatagcattg cgagacgctg gagccggagc accctatgtc     120
gcagtatctg tctttgattc ctgcctcatc ctattattta tcgcacctac gttcaatatt     180
acaggcgaac atacttacta aagtgtgtta attaattaat gcttgtagga cataataata     240
acaattgaat gtctgcacag ccactttcca cacagacatc ataacaaaaa atttccacca     300
aaccccccct ccccgcttc tggccacagc acttaaacac atctctgcca aaccccaaaa      360
acaaagaacc ctaaccag cctaaccaga tttcaaattt tatcttttgg cggtatgcac       420
ttttaacagt cacccccaa ctaacacatt attttcccct cccactccca tactactaat      480
ctcatcaata caaccccgc ccatcctacc agcacacac accgctgc taaccccata         540
ccccgaacca accaaacccc aaagacaccc cccacagttt atgtagctta cctcctcaaa     600
gcaatacact gaaaatgttt agacgggctc acatcacccc ataaacaaat aggtttggtc     660
ctagcctttc tattagctct tagtaagatt acacatgcaa gcatcccgt tccagtgagt      720
tcaccctcta atcaccacg atcaaaaggg acaagcatca agcacgcagc aatgcagctc      780
aaaacgctta gcctagccac accccacgg gaaacagcag tgattaacct ttagcaataa      840
acgaaagttt aactaagcta tactaacccc agggttggtc aatttcgtgc cagccaccgc     900
ggtcacacga ttaacccaag tcaatagaag ccggcgtaaa gagtgtttta gatcaccccc     960
tccccaataa agctaaaact cacctgagtt gtaaaaaact ccagttgaca caaaatagac    1020
tacgaaagtg gctttaacat atctgaacac acaaatgcta agacccaaac tgggattaga    1080
taccccacta tgcttagccc taaacctcaa cagttaaatc aacaaaactg ctcgccagaa    1140
cactacgagc cacagcttaa aactcaaagg acctggcggt gcttcatatc cctctagagg    1200
agcctgttct gtaatcgata aaccccgatc aacctcacca cctcttgctc agcctatata    1260
ccgccatctt cagcaaaccc tgatgaaggc tacaaagtaa gcgcaagtac ccacgtaaag    1320
acgttaggtc aaggtgtagc ccatgaggtg caagaaatg ggctacattt tctaccccag     1380
aaaactacga tagcccttat gaaacttaag ggtcgaaggt ggatttagca gtaaactaag    1440
agtagagtgc ttagttgaac agggccctga agcgcgtaca caccgcccgt caccctcctc    1500
aagtatactt caaaggacat ttaactaaaa cccctacgca tttatataga ggagacaagt    1560
cgtaacatgg taagtgtact ggaaagtgca cttggacgaa ccagagtgta gcttaacaca    1620
aagcacccaa cttacactta ggagatttca acttaacttg accgctctga gctaaaccta    1680
gccccaaacc cactccacct tactaccaga caaccttagc caaaccattt acccaaataa    1740
agtataggcg atagaaattg aaacctggcg caatagatat agtaccgcaa gggaaagatg    1800
aaaaattata accaagcata atatagcaag gactaacccc tatacctct gcataatgaa     1860
ttaactagaa ataactttgc aaggagagcc aaagctaaga cccccgaaac cagacgagct    1920
acctaagaac agctaaaaga gcacacccgt ctatgtagca aaatagtggg aagatttata    1980
ggtagaggcg acaaacctac cgagcctggt gatagctggt tgtccaagat agaatcttag    2040
ttcaactta aatttgccca cagaaccctc taaatcccct tgtaaattta actgttagtc     2100
caaagaggaa cagctctttg gacactagga aaaaccttg tagagagagt aaaaaattta    2160
acacccatag taggcctaaa agcagccacc aattaagaaa gcgttcaagc tcaacaccca    2220
```

```
ctacctaaaa aatcccaaac atataactga actcctcaca cccaattgga ccaatctatc    2280
accctataga agaactaatg ttagtataag taacatgaaa acattctcct ccgcataagc    2340
ctgcgtcaga ttaaaacact gaactgacaa ttaacagccc aatatctaca atcaaccaac    2400
aagtcattat taccctcact gtcaacccaa cacaggcatg ctcataagga aaggttaaaa    2460
aaagtaaaag gaactcggca aatcttaccc cgcctgttta ccaaaaacat cacctctagc    2520
atcaccagta ttagaggcac cgcctgccca gtgacacatg tttaacggcc gcggtaccct    2580
aaccgtgcaa aggtagcata atcacttgtt ccttaaatag ggacctgtat gaatggctcc    2640
acgagggttc agctgtctct tacttttaac cagtgaaatt gacctgcccg tgaagaggcg    2700
ggcataacac agcaagacga aagaccccta tggagcttta atttattaat gcaaacagta    2760
cctaacaaac ccacaggtcc taaactacca aacctgcatt aaaaatttcg gttgggcga    2820
cctcggagca gaacccaacc tccgagcagt acatgctaag acttcaccag tcaaagcgaa    2880
ctactatact caattgatcc aataacttga ccaacggaac aagttaccct agggataaca    2940
gcgcaatcct attctagagt ccatatcaac aatagggttt acgacctcga tgttggatca    3000
ggacatcccg atggtgcagc cgctattaaa ggttcgtttg ttcaacgatt aaagtcctac    3060
gtgatctgag ttcagaccgg agtaatccag gtcggtttct atctaccttc aaattcctcc    3120
ctgtacgaaa ggacaagaga aataaggcct acttcacaaa gcgccttccc cgtaaatga    3180
tatcatctca acttagtatt atacccacac ccacccaaga cagggtttg ttaagatggc    3240
agagcccggt aatcgcataa aacttaaaac tttacagtca gaggttcaat tcctcttctt    3300
aacaacatac ccatggccaa cctcctactc ctcattgtac ccattctaat cgcaatggca    3360
ttcctaatgc ttaccgaacg aaaaattcta ggctatatac aactacgcaa aggccccaac    3420
gttgtaggcc cctacgggct actacaaccc ttcgctgacg ccataaaact cttcaccaaa    3480
gagcccctaa aacccgccac atctaccatc accctctaca tcaccgcccc gaccttagct    3540
ctcaccatcg ctcttctact atgaaccccc ctccccatac ccaacccct ggtcaacctc    3600
aacctaggcc tcctatttat tctagccacc tctagcctag ccgtttactc aatcctctga    3660
tcagggtgag catcaaactc aaactacgcc ctgatcggcg cactgcgagc agtagcccaa    3720
acaatctcat atgaagtcac cctagccatc attctactat caacattact aataagtggc    3780
tcctttaacc tctccaccct tatcacaaca caagaacacc tctgattact cctgccatca    3840
tgacccttgg ccataatatg atttatctcc acactagcag agaccaaccg aacccccttc    3900
gaccttgccg aaggggagtc cgaactagtc tcaggcttca acatcgaata cgccgcaggc    3960
cccttcgccc tattcttcat agccgaatac acaaacatta ttataataaa caccctcacc    4020
actacaatct tcctaggaac aacatatgac gcactctccc ctgaactcta cacaacatat    4080
tttgtcacca agaccctact tctaacctcc ctgttcttat gaattcgaac agcatacccc    4140
cgattccgct acgaccaact catacacctc ctatgaaaaa acttcctacc actcacccta    4200
gcattactta tatgatatgt ctccatacc attacaatct ccagcattcc ccctcaaacc    4260
taagaaatat gtctgataaa agagttactt tgatagagta aataatagga gcttaaaccc    4320
ccttatttct aggactatga aatcgaacc catccctgag aatccaaaat tctccgtgcc    4380
acctatcaca ccccatccta agtaaggtc agctaaataa gctatcgggc ccataccccg    4440
aaaatgttgg ttatacccctt cccgtactaa ttaatcccct ggcccaaccc gtcatctact    4500
ctaccatctt tgcaggcaca ctcatcacag cgctaagctc gcactgattt ttacctgag    4560
taggcctaga aataaacatg ctagctttta ttccagttct aaccaaaaaa ataaaccctc    4620
```

```
gttccacaga agctgccatc aagtatttcc tcacgcaagc aaccgcatcc ataatccttc    4680
taatagctat cctcttcaac aatatactct ccggacaatg aaccataacc aatactacca    4740
atcaatactc atcattaata atcataatag ctatagcaat aaaactagga atagcccect    4800 ttcacttctg agtcccagag gttacccaag gcaccctct gacatccggc ctgcttcttc      4860
tcacatgaca aaaactagcc cccatctcaa tcatatacca aatctctccc tcactaaacg    4920
taagccttct cctcactctc tcaatcttat ccatcatagc aggcagttga ggtggattaa    4980
accagaccca gctacgcaaa atcttagcat actcctcaat tacccacata ggatgaataa    5040
tagcagttct accgtacaac cctaacataa ccattcttaa tttaactatt tatattatcc     5100
taactactac cgcattccta ctactcaact taaactccag caccacgacc ctactactat    5160
ctcgcacctg aaacaagcta acatgactaa cacccttaat tccatccacc ctcctctccc    5220
taggaggcct gccccgcta accggctttt tgcccaaatg ggccattatc gaagaattca     5280
caaaaaacaa tagcctcatc atccccacca tcatagccac catcaccctc cttaacctct    5340
acttctacct acgcctaatc tactccacct caatcacact actccccata tctaacaacg    5400
taaaaataaa atgacagttt gaacatacaa aacccacccc attcctcccc acactcatcg    5460
cccttaccac gctactccta cctatctccc cttttatact aataatctta tagaaattta    5520
ggttaaatac agaccaagag ccttcaaagc cctcagtaag ttgcaatact taatttctgt    5580
aacagctaag gactgcaaaa ccccactctg catcaactga acgcaaatca gccactttaa    5640
ttaagctaag cccttactag accaatggga cttaaaccca caaacactta gttaacagct    5700
aagcacccta atcaactggc ttcaatctac ttctcccgcc gccgggaaaa aaggcgggag    5760
aagccccggc aggtttgaag ctgcttcttc gaatttgcaa ttcaatatga aaatcacctc    5820
ggagctggta aaagaggcc taaccctgt ctttagattt acagtccaat gcttcactca      5880 gccatttac ctcaccccca ctgatgttcg ccgaccgttg actattctct acaaaccaca    5940
aagacattgg aacactatac ctattattcg gcgcatgagc tggagtccta ggcacagctc    6000
taagcctcct tattcgagcc gagctgggcc agccaggcaa ccttctaggt aacgaccaca    6060
tctacaacgt tatcgtcaca gcccatgcat ttgtaataat cttcttcata gtaatacca     6120 tcataatcgg aggctttggc aactgactag ttcccctaat aatcggtgcc cccgatatgg    6180
cgtttccccg cataaacaac ataagcttct gactcttacc tccctctctc ctactcctgc    6240
tcgcatctgc tatagtggag gccggagcag gaacaggttg aacagtctac cctcccttag    6300
cagggaacta ctcccacccct ggagcctccg tagacctaac catcttctcc ttacacctag    6360
caggtgtctc ctctatctta ggggccatca atttcatcac aacaattatc aatataaaac    6420
cccctgccat aacccaatac caaacgcccc tcttcgtctg atccgtccta atcacagcag    6480
tcctacttct cctatctctc ccagtcctag ctgctggcat cactatacta ctaacagacc    6540
gcaacctcaa caccaccttc ttcgaccccg ccggaggagg agaccccatt ctataccaac    6600
acctattctg attttcggt caccctgaag tttatattct tatcctacca ggcttcggaa    6660
taatctccca tattgtaact tactactccg gaaaaaaaga accatttgga tacataggta    6720
tggtctgagc tatgatatca attggcttcc tagggtttat cgtgtgagca caccatatat    6780
ttacagtagg aatagacgta gacacacgag catatttcac ctccgctacc ataatcatcg    6840
ctatccccac cggcgtcaaa gtatttagct gactcgccac actccacgga agcaatatga    6900
aatgatctgc tgcagtgctc tgagccctag gattcatctt tcttttcacc gtaggtggcc    6960
```

```
tgactggcat tgtattagca aactcatcac tagacatcgt actacacgac acgtactacg    7020
ttgtagccca cttccactat gtcctatcaa taggagctgt atttgccatc ataggaggct    7080
tcattcactg atttccccta ttctcaggct cacccctaga ccaaacctac gccaaaatcc    7140
atttcactat catattcatc ggcgtaaatc taactttctt cccacaacac tttctcggcc    7200
tatccggaat gccccgacgt tactcggact accccgatgc atacaccaca tgaaacatcc    7260
tatcatctgt aggctcattc atttctctaa cagcagtaat attaataatt ttcatgattt    7320
gagaagcctt cgcttcgaag cgaaaagtcc taatagtaga agaaccctcc ataaacctgg    7380
agtgactata tggatgcccc ccaccctacc acacattcga agaacccgta tacataaaat    7440
ctagacaaaa aaggaaggaa tcgaaccccc caaagctggt ttcaagccaa ccccatggcc    7500
tccatgactt tttcaaaaag gtattagaaa aaccatttca taactttgtc aaagttaaat    7560
tataggctaa atcctatata tcttaatggc acatgcagcg caagtaggtc tacaagacgc    7620 tacttccccct atcatagaag agcttatcac ctttcatgat cacgccctca taatcatttt    7680
ccttatctgc ttcctagtcc tgtatgccct tttcctaaca ctcacaacaa aactaactaa    7740
tactaacatc tcagacgctc aggaaataga aaccgtctga actatcctgc cgccatcat     7800 cctagtcctc atcgccctcc catccctacg catcctttac ataacagacg aggtcaacga    7860
tccctccctt accatcaaat caattggcca ccaatggtac tgaacctacg agtacaccga    7920
ctacggcgga ctaatcttca actcctacat acttccccca ttattcctag aaccaggcga    7980
cctgcgactc cttgacgttg acaatcgagt agtactcccg attgaagccc ccattcgtat    8040
aataattaca tcacaagacg tcttgcactc atgagctgtc cccacattag gcttaaaaac    8100
agatgcaatt cccggacgtc taaaccaaac cactttcacc gctacacgac cgggggtata    8160
ctacggtcaa tgctctgaaa tctgtggagc aaaccacagt ttcatgccca tcgtcctaga    8220
attaattccc ctaaaaatct ttgaaatagg gcccgtattt accctatagc accccctcta    8280 cccctctag agcccactgt aaagctaact tagcattaac cttttaagtt aaagattaag    8340
agaaccaaca cctctttaca gtgaaatgcc ccaactaaat actaccgtat ggcccaccat    8400
aattaccccc atactcctta cactattcct catcacccaa ctaaaaatat taaacacaaa    8460
ctaccaccta cctccctcac caaagcccat aaaaataaaa aattataaca acccctgaga    8520
accaaaatga cgaaaatct gttcgcttca ttcattgccc ccacaatcct aggcctaccc     8580
gccgcagtac tgatcattct atttccccct ctattgatcc ccacctccaa atatctcatc    8640
aacaaccgac taatcaccac ccaacaatga ctaatcaaac taacctcaaa acaaatgata    8700
accatacaca cactaaagg acgaacctga tctcttatac tagtatcctt aatcattttt    8760
attgccacaa ctaacctcct cggactcctg cctcactcat ttacaccaac cacccaacta    8820
tctataaacc tagccatggc catccccctta tgagcgggca cagtgattat aggctttcgc    8880
tctaagatta aaaatgccct agcccacttc ttaccacaag gcacacctac acccccttatc    8940 cccatactag ttattatcga aaccatcagc ctactcattc aaccaatagc cctggccgta    9000
cgcctaaccg ctaacattac tgcaggccac tactcatgc acctaattgg aagcgccacc     9060
ctagcaatat caaccattaa ccttccctct acacttatca tcttcacaat tctaattcta    9120
ctgactatcc tagaaatcgc tgtcgcctta atccaagcct acgttttcac acttctagta    9180
agcctctacc tgcacgacaa cacataatga cccaccaatc acatgcctat catatagtaa    9240
aacccagccc atgaccccta acaggggccc tctcagccct cctaatgacc tccggcctag    9300
ccatgtgatt tcacttccac tccataacgc tcctcatact aggcctacta accaacacac    9360
```

-continued

```
taaccatata ccaatgatgg cgcgatgtaa cacgagaaag cacataccaa ggccaccaca    9420
caccacctgt ccaaaaaggc cttcgatacg ggataatcct atttattacc tcagaagttt    9480
tttcttcgc aggattttc tgagcctttt accactccag cctagccct accccccaat      9540
taggagggca ctggccccca acaggcatca cccgctaaa tccctagaa gtcccactcc     9600
taaacacatc cgtattactc gcatcaggag tatcaatcac ctgagctcac catagtctaa    9660
tagaaaacaa ccgaaaccaa ataattcaag cactgcttat tacaatttta ctgggtctct    9720
attttaccct cctacaagcc tcagagtact tcgagtctcc cttcaccatt tccgacggca    9780
tctacggctc aacattttt gtagccacag gcttccacgg acttcacgtc attattggct     9840
caactttcct cactatctgc ttcatccgcc aactaatatt tcactttaca tccaaacatc    9900
actttggctt cgaagccgcc gcctgatact ggcattttgt agatgtggtt tgactatttc    9960
tgtatgtctc catcattga tgagggtctt actcttttag tataaatagt accgttaact   10020
tccaattaac tagttttgac aacattcaaa aaagagtaat aaacttcgcc ttaattttaa   10080
taatcaacac cctcctagcc ttactactaa taattattac attttgacta ccacaactca   10140
acggctacat agaaaaatcc accccttacg agtgcggctt cgaccctata tcccccgccc   10200
gcgtcccttt ctccataaaa ttcttcttag tagctattac cttcttatta tttgatctag   10260
aaattgccct ccttttaccc ctaccatgag ccctacaaac aactaacctg ccactaatag   10320
ttatgtcatc cctcttatta atcatcatcc tagccctaag tctggcctat gagtgactac   10380
aaaaaggatt agactgaacc gaattggtat atagtttaaa caaaacgaat gatttcgact   10440
cattaaatta tgataatcat atttaccaaa tgcccctcat ttacataaat attatactag   10500
catttaccat ctcacttcta ggaatactag tatatcgctc acacctcata tcctccctac   10560
tatgcctaga aggaataata ctatcgctgt tcattatagc tactctcata accctcaaca   10620
cccactccct cttagccaat attgtgccta ttgccatact agtctttgcc gcctgcgaag   10680
cagcggtggg cctagcccta ctagtctcaa tctccaacac atatggccta gactacgtac   10740
ataacctaaa cctactccaa tgctaaaact aatcgtccca acaattatat tactaccact   10800
gacatgactt tccaaaaaac acataatttg aatcaacaca accacccaca gcctaattat   10860
tagcatcatc cctctactat ttttaaccaa atcaacaac aacctattta gctgttcccc    10920
aaccttttcc tccgaccccc taacaaccccc cctcctaata ctaactacct gactcctacc   10980
cctcacaatc atggcaagcc aacgccactt atccagtgaa ccactatcac gaaaaaaact   11040
ctacctctct atactaatct ccctacaaat ctccttaatt ataacattca cagccacaga   11100
actaatcata ttttatatct tcttcgaaac cacacttatc cccaccttgg ctatcatcac   11160
ccgatgaggc aaccagccag aacgcctgaa cgcaggcaca tacttcctat tctacaccct   11220
agtaggctcc cttcccctac tcatcgcact aatttacact cacaacaccc taggctcact   11280
aaacattcta ctactcactc tcactgccca agaactatca aactcctgag ccaataactt   11340
aatatgacta gcttacacaa tagcttttat agtaaagata cctctttacg gactccactt   11400
atgactccct aaagcccatg tcgaagcccc catcgctggg tcaatagtac ttgccgcagt   11460
actcttaaaa ctaggcggct atggtataat acgcctcaca ctcattctca acccctgac    11520
aaaacacata gcctacccct tccttgtact atccctatga ggcataatta taacaagctc    11580
catctgccta cgacaaacag acctaaaatc gctcattgca tactcttcaa tcagccacat   11640
agccctcgta gtaacagcca ttctcatcca aaccccctga agcttcaccg gcgcagtcat   11700
```

```
tctcataatc gcccacgggc ttacatcctc attactattc tgcctagcaa actcaaacta   11760
cgaacgcact cacagtcgca tcataatcct ctctcaagga cttcaaactc tactcccact   11820
aatagctttt tgatgacttc tagcaagcct cgctaacctc gccttacccc ccactattaa   11880
cctactggga gaactctctg tgctagtaac cacgttctcc tgatcaaata tcactctcct   11940
acttacagga ctcaacatac tagtcacagc cctatactcc ctctacatat ttaccacaac   12000
acaatggggc tcactcaccc accacattaa caacataaaa ccctcattca cacgagaaaa   12060
caccctcatg ttcatacacc tatcccccat tctcctccta tccctcaacc ccgacatcat   12120
taccgggttt tcctcttgta aatatagttt aaccaaaaca tcagattgtg aatctgacaa   12180
cagaggctta cgacccctta tttaccgaga aagctcacaa gaactgctaa ctcatgcccc   12240
catgtctaac aacatggctt tctcaacttt taaaggataa cagctatcca ttggtcttag   12300
gccccaaaaa ttttggtgca actccaaata aaagtaataa ccatgcacac tactataacc   12360
accctaaccc tgacttccct aattcccccc atccttacca cctcgttaa ccctaacaaa    12420 aaaaactcat accccattta tgtaaaatcc attgtcgcat ccacctttat tatcagtctc   12480
ttccccacaa caatattcat gtgcctagac caagaagtta ttatctcgaa ctgacactga   12540
gccacaaccc aaacaaccca gctctcccta agcttcaaac tagactactt ctccataata   12600
ttcatccctg tagcattgtt cgttacatgg tccatcatag aattctcact gtgatatata   12660
aactcagacc caaacattaa tcagttcttc aaatatctac tcatcttcct aattaccata   12720
ctaatcttag ttaccgctaa caacctattc caactgttca tcggctgaga gggcgtagga   12780
attatatcct tcttgctcat cagttgatga tacgcccgag cagatgccaa cacagcagcc   12840
attcaagcaa tcctatacaa ccgtatcggc gatatcggtt tcatcctcgc cttagcatga   12900
tttatcctac actccaactc atgagaccca caacaaatag cccttctaaa cgctaatcca   12960
agcctcaccc cactactagg cctcctccta gcagcagcag gcaaatcagc ccaattaggt   13020
ctccacccct gactcccctc agccatagaa ggccccaccc cagtctcagc cctactccac   13080
tcaagcacta tagttgtagc aggaatcttc ttactcatcc gcttccaccc cctagcagaa   13140
aatagcccac taatccaaac tctaacacta tgcttaggcg ctatcaccac tctgttcgca   13200
gcagtctgcg cccttacaca aaatgacatc aaaaaaatcg tagccttctc cacttcaagt   13260
caactaggac tcataatagt tacaatcggc atcaaccaac cacacctagc attcctgcac   13320
atctgtaccc acgccttctt caaagccata ctatttatgt gctccgggtc catcatccac   13380
aaccttaaca atgaacaaga tattcgaaaa ataggaggac tactcaaaac catacctctc   13440
acttcaacct ccctcaccat tggcagccta gcattagcag gaatacccttt cctcacaggt   13500 ttctactcca aagaccacat catcgaaacc gcaaacatat catacacaaa cgcctgagcc   13560
ctatctatta ctctcatcgc tacctccctg acaagcgcct atagcactcg aataattctt   13620
ctcaccctaa caggtcaacc tcgcttcccc acccttacta acattaacga aaataacccc   13680
accctactaa accccattaa cgcctggca gccggaagcc tattcgcagg atttctcatt    13740
actaacaaca tttccccgc atcccccttc caaacaacaa tccccctcta cctaaaactc    13800
acagccctcg ctgtcacttt cctaggactt ctaacagccc tagacctcaa ctacctaacc   13860
aacaaactta aaataaaatc cccactatgc acatttttatt tctccaacat actcggattc   13920
taccctagca tcacacaccg cacaatcccc tatctaggcc ttcttacgag ccaaaacctg   13980
cccctactcc tcctagacct aacctgacta gaaaagctat tacctaaaac aatttcacag   14040
caccaaatct ccacctccat catcacctca acccaaaaag gcataattaa actttacttc   14100
```

```
ctctctttct tcttcccact catcctaacc ctactcctaa tcacataacc tattcccccg    14160
agcaatctca attacaatat atacaccaac aaacaatgtt caaccagtaa ctactactaa    14220
tcaacgccca taatcataca aagcccccgc accaatagga tcctcccgaa tcaaccctga    14280
cccctctcct tcataaatta ttcagcttcc tacactatta aagtttacca caaccaccac    14340
cccatcatac tctttcaccc acagcaccaa tcctacctcc atcgctaacc ccactaaaac    14400
actcaccaag acctcaaccc ctgaccccca tgcctcagga tactcctcaa tagccatcgc    14460
tgtagtatat ccaaagacaa ccatcattcc ccctaaataa attaaaaaaa ctattaaacc    14520
catataacct cccccaaaat tcagaataat aacacacccg accacaccgc taacaatcaa    14580
tactaaaccc ccataaatag gagaaggctt agaagaaaac cccacaaacc ccattactaa    14640
acccacactc aacagaaaca aagcatacat cattattctc gcacggacta caaccacgac    14700
caatgatatg aaaaaccatc gttgtatttc aactacaaga acaccaatga ccccaatacg    14760
caaaattaac cccctaataa aattaattaa ccactcattc atcgacctcc ccaccccatc    14820
caacatctcc gcatgatgaa acttcggctc actccttggc gcctgcctga tcctccaaat    14880
caccacagga ctattcctag ccatgcacta ctcaccagac gcctcaaccg ccttttcatc    14940
aatcgcccac atcactcgag acgtaaatta tggctgaatc atccgctacc ttcacgccaa    15000
tggcgcctca atattcttta tctgcctctt cctacacatc gggcgaggcc tatattacgg    15060
atcatttctc tactcagaaa cctgaaacat cggcattatc ctcctgcttg caactatagc    15120
aacagccttc ataggctatg tcctcccgtg aggccaaata tcattctgag gggccacagt    15180
aattacaaac ttactatccg ccatcccata cattgggaca gacctagttc aatgaatctg    15240
aggaggctac tcagtagaca gtcccaccct cacacgattc tttacctttc acttcatctt    15300
gcccttcatt attgcagccc tagcaacact ccacctccta ttcttgcacg aaacgggatc    15360
aaacaacccc ctaggaatca cctcccattc cgataaaatc accttccacc cttactacac    15420
aatcaaagac gccctcggct tacttctctt ccttctctcc ttaatgacat taacactatt    15480
ctcaccagac ctcctaggcg acccagacaa ttatacccta gccaaccccct taaacacccc    15540 tccccacatc aagcccgaat gatatttcct attcgcctac acaattctcc gatccgtccc    15600
taacaaacta ggaggcgtcc ttgccctatt actatccatc ctcatcctag caataatccc    15660
catcctccat atatccaaac aacaaagcat aatatttcgc ccactaagcc aatcacttta    15720
ttgactccta gccgcagacc tcctcattct aacctgaatc ggaggacaac cagtaagcta    15780
cccttttacc atcattggac aagtagcatc cgtactatac ttcacaacaa tcctaatcct    15840
aataccaact atctccctaa ttgaaaacaa aatactcaaa tgggcctgtc cttgtagtat    15900
aaactaatac accagtcttg taaccggaga tgaaaacctt ttttccaagg acaaatcaga    15960 gaaaagtct ttaactccac cattagcacc caaagctaag attctaatt aaactattct    16020 ctgttctttc atggggaagc agatttgggt accaccaag tattgactca cccatcaaca    16080
accgctatgt atttcgtaca ttactgccag ccaccatgaa tattgtacgg taccataaat    16140
acttgaccac ctgtagtaca taaaaaccca atccacatca aaaccccctc cccatgctta    16200
caagcaagta cagcaatcaa ccctcaacta tcacacatca actgcaactc caaagccacc    16260
cctcacccac taggatacca acaaacctac ccaccttaa cagtacatag tacataaagc    16320
```

-continued

```
catttaccgt acatagcaca ttacagtcaa atcccttctc gtccccatgg atgacccccc  16380
tcagataggg gtcccttgac caccatcctc cgtgaaatca atatcccgca caagagtgct  16440
actctcctcg ctccgggccc ataacacttg ggggtagcta aagtgaactg tatccgacat  16500
ctggttccta cttcagggtc ataaagccta aatagcccac acgttcccct taaataagac  16560
atcacgatg                                                          16569
```